(12) United States Patent
Cahoon et al.

(10) Patent No.: US 6,465,229 B2
(45) Date of Patent: *Oct. 15, 2002

(54) PLANT CAFFEOYL-COA O-METHYLTRANSFERASE

(75) Inventors: Rebecca E. Cahoon, Wilmington, DE (US); Gary M. Fader, Landenberg, PA (US); J. Antoni Rafalski, Wilmington, DE (US)

(73) Assignee: E. I. du Pont de Nemours and Company, Wilmington, DE (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/452,239

(22) Filed: Dec. 1, 1999

(65) Prior Publication Data

US 2002/0081693 A1 Jun. 27, 2002

Related U.S. Application Data

(60) Provisional application No. 60/110,594, filed on Dec. 2, 1998.

(51) Int. Cl.⁷ .................................. C12N 9/10
(52) U.S. Cl. ............... 435/193; 435/252.33; 435/320.1; 536/23.2
(58) Field of Search ........................... 435/193, 252.33, 435/320.1; 536/23.2

(56) References Cited

U.S. PATENT DOCUMENTS 5,728,570 A    3/1998  Matern et al. ........... 435/252.3

FOREIGN PATENT DOCUMENTS

| WO | WO 98/11205 | 3/1998 |
| WO | WO 99/09188 | 2/1999 |
| WO | WO 99/10498 | 3/1999 |

OTHER PUBLICATIONS

Vance, C. P. et al. (1980) Annu. Rev. Phytopathol. 18:259–288.
Inoue, K. et al. (1998) Plant Physiol. 117(3):761–770.
Kuhnl, T. et al. (1989) Plant Sci. 60:21–25.
Pakusch, A.E. et al. (1989) Arch. Biochem. Biophys. 271:488–494.
Z. H. et al. (1994) Plant Cell 6:1427–1439.
Boudet, A.M. et al. (1996) Mol Breeding 2:25–39.
Campbell, M. M. et al. (1996) Plant Physiol. 110:3–13.
Sewalt, V.J. H. et al. (1997) J. Agric. Food Chem. 45:1977–1983.
Sewalt, V.J.H. et al. (1997) Plant Physiol. 115:41–50.
NCBI General Identifier No. 2960356.
NCBI General Identifier No. 684942.
NCBI General Identifier No. 2511737.
NCBI General Identifier No. 1366552.
NCBI General Identifier No. 1679853.
Plant Phys. 113:1003 (1997).
NCBI General Identifier No. 701308.
NCBI General Identifier No. 700492.
NCBI General Identifier No. 701742.
NCBI General Identifier No. 3023436.
NCBI General Identifier No. 115559.
J. Biol. Chem. 266(26):17416–17423 (1991).
Plant Mol. Biol. 33(2):323–341 (1997).
Plant Phys. 95:137–143 (1991).
NCBI General Identifier No. 438897.
Plant Phys. 108(1):429–430 (1995).
J. Biosci. 22(2):161–175 (1997).
NCBI General Identifier No. 1679853.
NCBI General Identifier No. 3023432.
NCBI General Identifier No. 5091498.
Civardi et al. (1999) Plant Phys. 120:1206.
NCBI General Identifier No. 5101868.
NCBI General Identifier No. 6073074.
NCBI General Identifier No. 5752909.
NCBI General Identifier No. 5753226.
Martz et al. (1998) Plant Mol. Biol. 36:427–437.

*Primary Examiner*—Ponnathapu Achutamurthy
*Assistant Examiner*—Christian L. Fronda

(57) ABSTRACT

This invention relates to an isolated nucleic acid fragment encoding a caffeoyl-CoA O-methyltransferase. The invention also relates to the construction of a chimeric gene encoding all or a portion of the caffeoyl-CoA O-methyltransferase, in sense or antisense orientation, wherein expression of the chimeric gene results in production of altered levels of the caffeoyl-CoA O-methyltransferase in a transformed host cell.

14 Claims, 4 Drawing Sheets

```
SEQ ID NO:04   MATTATEAAPAQEQQANGN--GEQKTRHSEVGHKSLLKSDDLYQYILDTSVYPREPESMK
SEQ ID NO:06   MAAGGDDTT-IAQVHSGIDSS-------------NKTLLKSEALYKYVLDTSVLPHEPESMR
SEQ ID NO:08   MASAGAGEG--KETAAGSSLH--------------SKTLLKSQPLYQYILESTVFPREPDCLR
SEQ ID NO:12   MAEAASAAAAATTEQANGSSGGEQKTRHSEVGHKSLLKSDDLYQYILETSVYPREHECMK
SEQ ID NO:14   MTTGNGDAPVIKNAHSDIDST--------------NKTLLKSDALYKYVLDTTVLPREPECMR
SEQ ID NO:18   MAEQ--------------NQNQTT-EAGRHQEVGHKSLLQSDALYQYILETSVYPREPESMK
SEQ ID NO:22   MA----------------NEEEQKNHLFGIKDLGHKTLLQSDALYQYILETSVYPREHECLK
SEQ ID NO:26   MTVI--------------KEEQQPNQIAGHKELGHKSLLQSDALYQYILETSVYPREHESLK
SEQ ID NO:28   MEN---------IKDPSIYRN-------------PVILQSEDLTKYILETAVYPREPAPLK
SEQ ID NO:32   MSS---------------N---------------PVILQSVNLTKYILETSVYPREEETLK
SEQ ID NO:38   MATTATEAAPAQEQQANGN--GEQKTRHSEVGHKSLLKSDDLYQYILDTSVYPREPESMK
SEQ ID NO:42   MATTAADATAAAPKD-QPANGSEQVTRHSEVGHKSLLQSDALYQYILETSVYPREHECMK
SEQ ID NO:46   MAPNGDNT--VANVHSGIDST--------------NKTLLKSDALYTYILDTTVFPREHECMR
SEQ ID NO:49   MATTATEAAPAQEQQANGN--GEQKTRHSEVGHKSLLKSDDLYQYILDTSVYPREPESMK
SEQ ID NO:50   MATN--------------GEEQQS-QAGRHQEVGHKSLLQSDALYQYILETSVYPREPECMK
               1                                                         60
               *                 *    *                 *  ** ******  *  *

SEQ ID NO:04   ELREITAKHPWN----LMTTSADEGQFLNMLIKLIGAKKTMEIGVYTGYSLLATALALPE
SEQ ID NO:06   ELRLVTDKHEWG----FMQSSPDEASLLRMLIKLSGARRTLEVGVFTGYSLLATALALPA
SEQ ID NO:08   ELRVATATHPMA----GMAASPDEVQLLQLLIEILGAKNAIEVGVFTGYSLLATALALPD
SEQ ID NO:12   ELREVTANHPWN----LMTTSADEGQFLNLLLKLIGAKKTMEIGVYTGYSLLATALAIPD
SEQ ID NO:14   DLRLLITDKHQWG----FMQSSADEAQLLGMLLKMAGAKRTIEVGVFTGYSLLATALALPE
SEQ ID NO:18   ELRELTAKHPWN----IMTTSADEGQFLNMLLKLINAKNTMEIGVYTGYSLLATALALPE
               *                         *  ***  *** ******
```

FIG. 1A

```
SEQ ID NO:22    ELRKMTAKHPLN----IMATPADEGQLLSMLVKLTNSKNALEIGVFTGYSLLSTALALPP
SEQ ID NO:26    ELRELTEKHPWN----LMATPPDEGQLLGMLLKLINAKNTMEIGVFTGYSLLSTALALPS
SEQ ID NO:28    ELREATNNHPWG----FIATLPEAGQLMTLLLKLLNPKKTIEVGVFTGYSLLLTALNIPH
SEQ ID NO:32    ELRKATAGHPWG----FMGAAPDAGQLMTLLLKLLNAKKTIEVGVFTGYSLLLTALTIPD
SEQ ID NO:38    ELREITAKHPWN----LMTTSADEGQFLNMLIKLIGAKKTMEIGVYTGYSLLATALALPE
SEQ ID NO:42    ELREITANHPWN----LMTTSADEGQFLNMLLKLIGAKKTMEIGVYTGYSLLATALAIPD
SEQ ID NO:46    DLRLITDKHPWG----YMQSSSDEAQLLGMLIKMAGAKKTIEVGVFTGYSLLATALALPE
SEQ ID NO:49    ELREVTAKHPWN----LMTTSADEGQFLNMLIKLIGAKKTMEIGVYTGYSLLATALALPE
SEQ ID NO:50    ELREVTAKHPWN----IMTTSADEGQFLNMLLKLVNAKNTMEIGVYTGYSLLATALAIPE
                                                                         120
                 **    *   *             *       *     *  *  *      *    **

SEQ ID NO:04    DGTILAMDINRENYE-LGLPCIEKAGVAHKIDFREGPALPVLDDLIAEEKNHG----SFDF
SEQ ID NO:06    DGKVIAFDVSREYYD-IGRPLIERAGVAGKVDFREGPALEQLDELLADPANHG----AFDF
SEQ ID NO:08    DGKIVAIDVTRESYDQIGSPVIEKAGVAHKIDFRVGLALPVLDQMVAEEGNKGK---FDF
SEQ ID NO:12    DGTILAMDINRENYE-LGLPSIEKAGVAHKIDFREGPALPVLDQLVEEEGNHG----SFDF
SEQ ID NO:14    DGKVVAIDPDRESYE-IGRPFLEKAGVAHKVDFPRGXGLEKLDELLAEEAAAGREAAAFDF
SEQ ID NO:18    DGKILAMDINRENYE-LGLPVIKKAGVDHKIEFREGPALPVLDEMIKDEKNHG----SYDF
SEQ ID NO:22    DGKILALDVNREYYE-LGLPIIQKAGVAHKIEFREGPALPFLDEMLKDENKKG----SLDF
SEQ ID NO:26    DGKILAMDVNREYYE-LGLPVIEKAGVAHKIDFREGPALPLLDVLIKDEKNKG----AFDF
SEQ ID NO:28    DGKITAIDINRKTYE-VGLPVIKKAGVEHKIDFIESPALPILDKLLEDPANEG----SFDF
SEQ ID NO:32    DGKIIALDPDRETYE-IGLPFIKKAGVEHKIDFIESPALPVLDKLVEDPSNKE----SFDF
SEQ ID NO:38    DGTILAMDINRENYE-LGLPCIEKAGVAHKIDFREGPALPVLDDLIAEEKNHG----SFDF
SEQ ID NO:42    DGTILAMDINRENYE-LGLPCIEKAGVAHKIDFREGPALPVLDALLEDEANHG----TFDF
SEQ ID NO:46    DGKVVAIDTDRECYE-VGRPFIEKAGMAHKVDFREGTGLARLDELLVEDDGA----ASYDF
```

FIG. 1B

```
SEQ ID NO:49    DGTILAMDINRENYE-LGLPCIEKAGVAHKIDFREGPALPVLDDLIAEEKNHG---SFDF
SEQ ID NO:50    DGKILAMDINRENYE-LGLPVIQKAGVAHKIDFKEGPALPVLDQMIEDGKYHG---SFDF
                                                                            180
                 **    ******* *** *     ***** ** * ****** *           ****

SEQ ID NO:04    VFVDADKDNYLNYHERLLKLIVKLGGLIGYDNTLWNGSVVLPDDAPMRKYIRFYRDFVLVL
SEQ ID NO:06    AFVDAHKPNYVRYHEQLLRLVRVGGTVVYDNTLWAGTVALPPDAPLSDLDRRFSAAIREL
SEQ ID NO:08    AFVDADKVNFLNYHERLLQLLRVGGLIAYDNTLWGGSVAASPDEPLSERDRALAVTTREF
SEQ ID NO:12    VFVDADKDNYLNYHERLMKLVKVGGLVGYDNTLWNGSVVLPADAPMRKYIRYYRDFVLEL
SEQ ID NO:14    AFVDADKPNYVKYHEQLLQLVRVGGHIVYDNTLWAGTVALPPDTPLSDLDRRFSVAIRDL
SEQ ID NO:18    IFVDADKDNYLNYHKRLIELVKVGGVIGYDNTLWNGSVVAPPDAPLRKYVRYRDFVLEL
SEQ ID NO:22    VFVDADKDNYLNYHKRLIELVKLGGLIGYDNTLWAGSVAAPPDAPLMDYIKPLRGHVMEL
SEQ ID NO:26    IYVDADKDNYLNYHKRVIELVKLGGLIGYDNTLWNGSVVAPPDAPLMDYVKYYRDFVMEL
SEQ ID NO:28    AFIDADKENYVNYHERLIKLVKLGGLIIYDNTLWGGRVCWP-EDKVPPHARSGRDAAIEF
SEQ ID NO:32    AFVDADKDNYWNYHERLLKLVKIGGLIIYDNTLWGGTVAWP-EEDVPVPKRKFRQATLAF
SEQ ID NO:38    VFVDADKDNYLNYHERLLKLVKLGGLIGYDNTLWNGSVVLPDDAPMRKYIRFYRDFVLVL
SEQ ID NO:42    VFVDADKDNYLNYHERLMKLVKLGGLLGYDNTLWNGSVVLPADAPMRKYIRYYRDFVLDL
SEQ ID NO:46    AFVDADKPNYVRYHEQLLKLVRVGGTIIYDNTLWGGTVALPAGTPMSDLDTRFSAALRDL
SEQ ID NO:49    VFVDADKDNYLNYHERLLKLVKLGGLIGYDNTLWNGSVVLPDDAPMRKYIRFYRDFVLVL
SEQ ID NO:50    IFVDADKDNYINYHKRLIELVKVGGLIGYDNTLWNGSVVAPPDAPMRKYVRYRDFVLEL
                                                                            240
                 * ***   *  *** * *  *  **   ****           *       ***

SEQ ID NO:04    NKALAADDRVEICQLPVGDGVTLCRRVK.
SEQ ID NO:06    NVRLSQDPRVEVCQLAIADGVTICRRVV.
SEQ ID NO:08    NAAVAADPRVHVCQVAIADGLTLCRRVA.
SEQ ID NO:12    NKALAADHRVEICQLPVGDGITLCRRVK.
SEQ ID NO:14    NSRLAADPRIDVCQLAIADGITICRRLV.
SEQ ID NO:18    NKALAVDPRIEICMLPVGDGITICRRIK.
SEQ ID NO:22    NKYLAQDSRIEICQLPVGDGITLCRRII.
SEQ ID NO:26    NKALALDSRVEICQLPVGDGITLCRRII.
                 *      *  * *   * **  * ***
```

FIG. 1C

```
241                                                             269
SEQ ID NO:28  NKTITNDSRVEFALTSVGDGLNICRRVA.
SEQ ID NO:32  NKAIADDSRVEISVVSIGDGFTICRRAH.
SEQ ID NO:38  NKALAADDRVEICQLPVGDGVTLCRRVK.
SEQ ID NO:42  NKALAADQRVEICQLPVGDGITLCRRAK.
SEQ ID NO:46  NAKLAADPRIEVCQLAIADGVTICRRIV.
SEQ ID NO:49  NKALAADDRVEICQLPVGDGVTLCRRV-K
SEQ ID NO:50  NKALAADPRIEICMLPVGDGITLCRRIQ-
```

FIG. 1D

PLANT CAFFEOYL-COA O-METHYLTRANSFERASE

This application claims the benefit of U.S. Provisional Application No. 60/110,594, filed Dec. 2, 1998.

FIELD OF THE INVENTION

This invention is in the field of plant molecular biology. More specifically, this invention pertains to nucleic acid fragments encoding caffeoyl-CoA O-methyltransferase in plants and seeds.

BACKGROUND OF THE INVENTION

Plant cells and tissues can respond to mechanical, chemical or pathogen induced injury by producing various phenolic compounds including mono- or dimethoxylated lignin precursors via a complex series of biochemical reactions. These lignin precursors are eventually used by the plant to produce lignin which helps repair wounds by adding (i) hydrophobicity, a physical barrier against pathogen infection, and (ii) mechanical strength to the injured tissue (Vance, C. P. et al. (1980) *Annu Rev Phytopathol* 18:25–288). Biosynthesis of the mono- or dimethoxylated lignin precursors occurs, in part, by the action of two enzymes, caffeic acid 3-O-methyltransferase (COMT) and caffeoyl CoA 3-O-methyltransferase (CCOMT). Studies ave shown that the activities of these two enzymes increases prior to lignin deposition (Inoue, K. et al. (1998) *Plant Physiol* 117(3):761–770). Caffeoyl CoA 3-O-methyltransferase not only has been implicated in the synthesis of components during a plant's defense response (Kühnl, T., et al. (1989) *Plant Sci* 60:21–25; Pakusch, A. E. et al., (1989) *Arch Biochem Biophys* 271:488–494) but may also play a role in cell differentiation of meristematic tissue to form tracheary elements (Ye, Z. H. et al. (1994) *Plant Cell* 6:1427–1439). In the final state of differentiation of tracheary elements, only the cell wall remains to form a vascular tissue through which water and solutes circulate throughout the plant. Thus lignin is a vital component of the plants cell wall architecture and plays a role in host defence and injury repair mechanisms.

Because of lignin's importance in cell wall architecture and wound repair mechanisms there is considerable interest in the prospects for altering lignin quantity or quality by genetic engineering. For example, chemical treatments needed to remove lignin during the paper- pulping process are expensive and environmentally unfriendly. Plants with altered lignin quantity or quality could benefit this industry (Boudet, A. M. et al. (1996) *Mol Breeding* 2:25–39; Campbell, M. M. et al. (1996) *Plant Physiol* 110:3–13; Sewalt, V. J. H. et al. (1997) *J Agric Food Chem* 45:1977–1983; Sewalt V. J. H. et al. (1997) *Plant Physiol* 115:41–50). Thus, there is a great deal of interest in identifying the genes that encode proteins involved in the production of lignin in plants. Amino acid sequences of caffeoyl CoA 3-O-methyltransferase and encoding nucleotide sequences are available in the public domain (WO 9910498-A2; DE4117747-A; WO 9909188-A2; WO 9811205-A2). Caffeoyl-CoA O-methyltransferase genes appear to be part of a multigene family. These genes may be used in plant cells to control lignin production. Accordingly, the availability of nucleic acid sequences encoding all or a portion of an enzyme involved in the production of lignin would facilitate studies to better understand lignin production in plant cells and provide genetic tools to enhance or otherwise alter lignin biosynthesis which in turn could provide mechanisms to control cell wall architecture and host defence and injury repair mechanisms in plant cells.

SUMMARY OF THE INVENTION

The present invention relates to isolated polynucleotides comprising a nucleotide sequence encoding a first polypeptide of at least 50 amino acids that has at least 80% identity based on the Clustal method of alignment when compared to a polypeptide selected from the group consisting of a corn caffeoyl-CoA O-methyltransferase polypeptide of SEQ ID NO:8, a soybean caffeoyl-CoA O-methyltransferase polypeptide of SEQ ID NO:28, a soybean caffeoyl-CoA O-methyltransferase polypeptide of SEQ ID NO:30, a soybean caffeoyl-CoA O-methyltransferase polypeptide of SEQ ID NO:32, a soybean caffeoyl-CoA O-methyltransferase polypeptide of SEQ ID NO:34, and a wheat caffeoyl-CoA O-methyltransferase polypeptide of SEQ ID NO:48. The present invention also relates to isolated polynucleotides comprising a nucleotide sequence encoding a first polypeptide of at least 50 amino acids that has at least 95% identity based on the Clustal method of alignment when compared to a corn caffeoyl-CoA O-methyltransferase polypeptide of SEQ ID NO:2. The present invention also relates to isolated polynucleotides comprising a nucleotide sequence encoding a first polypeptide of at least 100 amino acids that has at least 80% identity based on the Clustal method of alignment when compared to a polypeptide selected from the group consisting of a rice caffeoyl-CoA O-methyltransferase polypeptide of SEQ ID NO:16, a soybean caffeoyl-CoA O-methyltransferase polypeptide of SEQ ID NO:20, a wheat caffeoyl-CoA O-methyltransferase polypeptide of SEQ ID NO:44, and a wheat caffeoyl-CoA O-methyltransferase polypeptide of SEQ ID NO:46. The present invention also relates to isolated polynucleotides comprising a nucleotide sequence encoding a first polypeptide of at least 100 amino acids that has at least 85% identity based on the Clustal method of alignment when compared to a polypeptide selected from the group consisting of a soybean caffeoyl-CoA O-methyltransferase polypeptide of SEQ ID NO:24 and a soybean caffeoyl-CoA O-methyltransferase polypeptide of SEQ ID NO:26. The present invention also relates to isolated polynucleotides comprising a nucleotide sequence encoding a first polypeptide of at least 100 amino acids that has at least 90% identity based on the Clustal method of alignment when compared to a polypeptide selected from the group consisting of a rice caffeoyl-CoA O-methyltransferase polypeptide of SEQ ID NO:10, a wheat caffeoyl-CoA O-methyltransferase polypeptide of SEQ ID NO:36, and a wheat caffeoyl-CoA O-methyltransferase polypeptide of SEQ ID NO:40. The present invention also relates to isolated polynucleotides comprising a nucleotide sequence encoding a first polypeptide of at least 150 amino acids that has at least 80% identity based on the Clustal method of alignment when compared to a rice caffeoyl-CoA O-methyltransferase polypeptide of SEQ ID NO:14. The present invention also relates to isolated polynucleotides comprising a nucleotide sequence encoding a first polypeptide of at least 150 amino acids that has at least 85% identity based on the Clustal method of alignment when compared to a corn caffeoyl-CoA O-methyltransferase polypeptide of SEQ ID NO:6. The present invention also relates to isolated polynucleotides comprising a nucleotide sequence encoding a first polypeptide of at least 150 amino acids that has at least 95% identity based on the Clustal method of alignment when compared to a corn caffeoyl-CoA O-methyltransferase polypeptide of SEQ ID NO:42. The present invention also relates to an isolated polynucleotide comprising the complement of the nucleotide sequences described above.

It is preferred that the isolated polynucleotides of the claimed invention consist of a nucleic acid sequence selected from the group consisting of SEQ ID NOs: 1, 5, 7, 9, 13, 15, 19, 23, 25, 27, 29, 31, 33, 35, 39, 41, 43, 45, and 47 that codes for the polypeptide selected from the group consisting of SEQ ID NOs: 1, 5, 7, 9, 13, 15, 19, 2, 6, 8, 10, 14, 16, 20, 24, 26, 28, 30, 32, 34, 36, 40, 42, 44, 46, and 48. The present invention also relates to an isolated polynucleotide comprising a nucleotide sequences of at least one of 40 (preferably at least one of 30) contiguous nucleotides derived from a nucleotide sequence selected from the group consisting of SEQ ID NOs:1, 5, 7, 9, 13, 15, 19, 23, 25, 27, 29, 31, 33, 35, 39, 41, 43, 45, and 47 and the complement of such nucleotide sequences.

The present invention relates to a chimeric gene comprising an isolated polynucleotide of the present invention operably linked to suitable regulatory sequences.

The present invention relates to an isolated host cell comprising a chimeric gene of the present invention or an isolated polynucleotide of the present invention. The host cell may be eukaryotic, such as a yeast or a plant cell, or prokaryotic, such as a bacterial cell. The present invention also relates to a virus, preferably a baculovirus, comprising an isolated polynucleotide of the present invention or a chimeric gene of the present invention.

The present invention relates to a process for producing an isolated host cell comprising a chimeric gene of the present invention or an isolated polynucleotide of the present invention, the process comprising either transforming or transfecting an isolated compatible host cell with a chimeric gene or isolated polynucleotide of the present invention.

The present invention relates to a caffeoyl-CoA O-methyltransferase polypeptide of at least 50 amino acids comprising at least 80% homology based on the Clustal method of alignment compared to a polypeptide selected from the group consisting of SEQ ID NOs:8, 28, 30, 32, 34, and 48. The present invention also relates to a caffeoyl-CoA O-methyltransferase polypeptide of at least 50 amino acids comprising at least 95% homology based on the Clustal method of alignment compared to a polypeptide f SEQ ID NO:2. The present invention also relates to a caffeoyl-CoA O-methyltransferase polypeptide of at least 100 amino acids comprising at least 80% homology based on the Clustal method of alignment compared to a polypeptide selected from the group consisting of SEQ ID NOs: 16, 20, 44, and 46. The present invention also relates to a caffeoyl-CoA O-methyltransferase polypeptide of at least 100 amino acids comprising at least 85% homology based on the Clustal method of alignment compared to a polypeptide selected from the group consisting of SEQ ID NOs:24 and 26. The present invention also relates to a caffeoyl-CoA O-methyltransferase polypeptide of at least 100 amino acids comprising at least 90% homology based on the Clustal method of alignment compared to a polypeptide selected from the group consisting of SEQ ID NOs:10, 36, and 40. The present invention also relates to a caffeoyl-CoA O-methyltransferase polypeptide of at least 150 amino acids comprising at least 80% homology based on the Clustal method of alignment compared to a polypeptide f SEQ ID NO:14. The present invention also relates to a caffeoyl-CoA O-methyltransferase polypeptide of at least 150 amino acids comprising at least 85% homology based on the Clustal method of alignment compared to a polypeptide f SEQ ID NO:6. The present invention also relates to a caffeoyl-CoA O-methyltransferase polypeptide of at least 150 amino acids comprising at least 95% homology based on the Clustal method of alignment compared to a polypeptide f SEQ ID NO:42.

The present invention relates to a method of selecting an isolated polynucleotide that affects the level of expression of a caffeoyl-CoA O-methyltransferase polypeptide in a plant cell, the method comprising the steps of:

constructing an isolated polynucleotide of the present invention or an isolated chimeric gene of the present invention;

introducing the isolated polynucleotide or the isolated chimeric gene into a plant cell;

measuring the level of a caffeoyl-CoA O-methyltransferase polypeptide in the plant cell containing the isolated polynucleotide; and comparing the level of a caffeoyl-CoA O-methyltransferase polypeptide in the plant cell containing the isolated polynucleotide with the level of a caffeoyl-CoA O-methyltransferase polypeptide in a plant cell that does not contain the isolated polynucleotide.

The present invention relates to a method of obtaining a nucleic acid fragment encoding a substantial portion of a caffeoyl-CoA O-methyltransferase polypeptide gene, preferably a plant caffeoyl-CoA O-methyltransferase polypeptide gene, comprising the steps of: synthesizing an oligonucleotide primer comprising a nucleotide sequence of at least one of 40 (preferably at least one of 30) contiguous nucleotides derived from a nucleotide sequence selected from the group consisting of SEQ ID NOs:1, 5, 7, 9, 13, 15, 19, 23, 25, 27, 29, 31, 33, 35, 39, 41, 43, 45, and 47 and the complement of such nucleotide sequences; and amplifying a nucleic acid fragment (preferably a cDNA inserted in a cloning vector) using the oligonucleotide primer. The amplified nucleic acid fragment preferably will encode all or a portion of a caffeoyl-CoA O-methyltransferase amino acid sequence.

The present invention also relates to a method of obtaining a nucleic acid fragment encoding all or a substantial portion of the amino acid sequence encoding a caffeoyl-CoA O-methyltransferase polypeptide comprising the steps of: probing a cDNA or genomic library with an isolated polynucleotide of the present invention; identifying a DNA clone that hybridizes with an isolated polynucleotide of the present invention; isolating the identified DNA clone; and sequencing the cDNA or genomic fragment that comprises the isolated DNA clone.

BRIEF DESCRIPTION OF THE DRAWING AND SEQUENCE DESCRIPTIONS

The invention can be more fully understood from the following detailed description and the accompanying drawing and Sequence Listing which form a part of this application.

FIG. 1 depicts the amino acid alignment between the caffeoyl-CoA O-methyltransferase encoded by the nucleotide sequences derived from corn clone cr1n.pk0002.c6 (SEQ ID NO:4), contig assembled from corn clones cbn10.pk0030.a9, cbn10.pk0058.e4, cepe7.pk0012.c4, cpk1c.pk001.h21, cr1n.pk0098.f2, cr1n.pk0158.c3, cr1n.pk0170.d8, cr1s.pk014.c4, and cta1n.pk0009.e4(SEQ ID NO:6), contig assembled from corn clones cen3n.pk0060.b10, cen3n.pk0125.b2, cepe7.pk0028.h4, cho1c.pk003.a13, cr1n.pk0171.e4, and csi1n.pk0020.c11 (SEQ ID NO:8), rice clone rl0n.pk085.k12 (SEQ ID NO:12), contig assembled from rice clones rlr24.pk0093.a3, rr1.pk0043.g9, rr1.pk0047.g8, and rsl1n.pk001.o7 (SEQ ID NO:14), contig assembled from soybean clones sdp2c.pk002.j20, sdp3c.pk011.m2, src.2c.pk002.g14, sre.pk0002.c9, sre.pk0002.f9, and sre.pk0044.c3 (SEQ ID NO:18), soybean clone sgs4c.pk003.d5 (SEQ ID NO:22), soybean clone src2c.pk003.b20 (SEQ ID NO:26), contig assembled from soybean clones sgc3c.pk001.17, sl2pk0046.g8, sl2pk0088.g6, sl2pk122.115, and sls1c.pk009.j22)SEQ ID NO:28), soybean clone sfl1.pk0006.a7 (SEQ ID NO:32), wheat clone wl1n.pk0141.a9 (SEQ ID NO:38), wheat clone w1m96.pk036.e8 (SEQ ID NO:42), wheat clone wlm96.pk037.m21 (SEQ ID NO:46), caffeoyl-CoA O-methyltransferase-encoding nucleic acid fragment from Zea mays (NCBI General Identification No. 5101868) (SEQ ID NO:49), and caffeoyl-CoA O-methyltransferase-encoding nucleic acid fragment from *Populus tremuloides* (NCBI General Identification No. 3023436) (SEQ ID NO:50). Amino acids which are conserved among all and at least two sequences with an amino acid at that position are indicated with an asterisk (*) above them. Dashes are used by the program to maximize alignment of the sequences.

Table 1 lists the polypeptides that are described herein, the designation of the cDNA clones that comprise the nucleic acid fragments encoding polypeptides representing all or a substantial portion of these polypeptides, and the corresponding identifier (SEQ ID NO:) as used in the attached Sequence Listing. Table 1 also identifies the cDNA clones as individual ESTs ("EST"), the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"). Nucleotide SEQ ID NOs:1, 5, 7, 9, 13, 17, 19, 23, 27, 29, 33, 35, 39, 43, and 47 correspond to nucleotide SEQ ID NOs:1, 11, 19, 3, 13, 5, 15, 21, 25, 27, 29, 7, 9, 17, and 23, respectively, presented in U.S. Provisional Application No. 60/110,594, filed Dec. 2, 1998. Amino acid SEQ ID NOs:2, 6, 8, 10, 14, 18, 20, 24, 28, 30, 34, 36, 40, 44, and 48 correspond to amino acid SEQ ID NOs:2, 12, 20, 4, 14, 6, 16, 22, 26, 28, 30, 8, 10, 18, and 24, respectively presented in U.S. Provisional Application No. 60/110,594, filed Dec. 2, 1998. The sequence descriptions and Sequence Listing attached hereto comply with the rules governing nucleotide and/or amino acid sequence disclosures in patent applications as set forth in 37 C.F.R. §1.821–1.825.

TABLE 1

Plant Caffeoyl-CoA O-Methyltransferase (CCOMT)

| Protein | Clone Designation | Status | SEQ ID NO: (Nucleotide) | SEQ ID NO: (Amino Acid) |
|---|---|---|---|---|
| CCOMT (Corn) | Contig of:<br>cr1n.pk0002.c6<br>cr1n.pk0063.c9<br>cr1n.pk0153.b2<br>cr1n.pk0168.h5<br>cr1n.pk0179.e10 | Contig | 1 | 2 |
| CCOMT (Corn) | cr1n.pk0002.c6:fis | CGS | 3 | 4 |
| CCOMT (Corn) | Contig of:<br>cbn10.pk0030.a9<br>cbn10.pk0058.e4<br>cepe7.pk0012.c4<br>cpk1c.pk001.h21<br>cr1n.pk0098.f2<br>cr1n.pk0158.c3<br>cr1n.pk0170.d8 | CGS | 5 | 6 |

TABLE 1-continued

Plant Caffeoyl-CoA O-Methyltransferase (CCOMT)

| Protein | Clone Designation | Status | SEQ ID NO: (Nucleotide) | SEQ ID NO: (Amino Acid) |
|---|---|---|---|---|
| CCOMT (Corn) | cr1s.pk014.c4<br>cta1n.k0009.e4<br>Contig of:<br>cen3n.pk0060.b10<br>cen3n.pk0125.b2<br>cepe7.pk0028.h4<br>cho1c.pk003.a13<br>cr1n.pk0171.e4<br>csi1n.pk0020.c11 | CGS | 7 | 8 |
| CCOMT (Rice) | r10n.pk085.k12<br>r1s24.pk0021.b11<br>r10n.pk091.11 | Contig | 9 | 10 |
| CCOMT (Rice) | r10n.pk085.k12:fis | CGS | 11 | 12 |
| CCOMT (Rice) | Contig of:<br>r1r24.pk0093.a3<br>rr1.pk0043.g9<br>rr1.pk0047.g8<br>rs11n.pk001.o7 | CGS | 13 | 14 |
| CCOMT (Rice) | Contig of:<br>r10n.pk082.i11<br>r1r48.pk0039.b7 | Contig | 15 | 16 |
| CCOMT (Soybean) | Contig of:<br>sdp2c.pk002.j20<br>sdp3c.pk011.m2<br>src2c.pk002.g14<br>sre.pk0002.c9<br>sre.pk0002.f9<br>sre.pk0044.c3 | CGS | 17 | 18 |
| CCOMT (Soybean) | Contig of:<br>sdp2c.pk014.j8<br>sf11.pk135.h3<br>sgs4c.pk003.d5<br>sr1.pk0077.h10<br>src2c.pk003.e4 | CGS | 19 | 20 |
| CCOMT (Soybean) | sgs4c.pk003.d5:fis | CGS | 21 | 22 |
| CCOMT (Soybean) | Contig of:<br>s12.pk0100.a8<br>src2c.pk001.o12<br>src2c.pk003.b20<br>src2c.pk010.f17 | CGS | 23 | 24 |
| CCOMT (Soybean) | src2c.pk003.b20:fis | CGS | 25 | 26 |
| CCOMT (Soybean) | Contig of:<br>sgc3c.pk001.17<br>s12.pk0046.g8<br>s12.pk0088.g6<br>s12.pk122.115<br>sls1c.pk009.j22 | CGS | 27 | 28 |
| CCOMT (Soybean) | sfl1.pk0006.a7:fis<br>sfl1n1.pk001.a9 | Contig | 29 | 30 |
| CCOMT (Soybean) | sfl1.pk0006.a7 | CGS | 31 | 32 |
| CCOMT (Soybean) | sls1c.pk008.g24 | EST | 33 | 34 |
| CCOMT (Wheat) | Contig of:<br>wl1n.pk0010.f2<br>wl1n.pk0140.h9<br>wl1n.pk0141.a9<br>wle1n.pk0035.g8<br>wle1n.pk0083.e5<br>wlk1.pk0006.b2<br>wlm96.pk033.j2<br>wre1n.pk0062.h9<br>wre1n.pk0112.d4 | Contig | 35 | 36 |
| CCOMT (Wheat) | wl1n.pk0141.a9:fis | CGS | 37 | 38 |
| CCOMT (Wheat) | Contig of:<br>wdk2c.pk006.k18<br>wlk1.pk0020.g6<br>wlm96.pk036.e8<br>wlrnk1.pk0016.g9<br>wlmk1.pk0017.e5 | Contig | 39 | 40 |
| CCOMT (Wheat) | wlm96.pk036.e8:fis | CGS | 41 | 42 |
| CCOMT (Wheat) | Contig of:<br>wle1n.pk0014.d12<br>wlm96.pk037.m21 | CGS | 43 | 44 |

TABLE 1-continued

Plant Caffeoyl-CoA O-Methyltransferase (CCOMT)

| | | | SEQ ID NO: | |
|---|---|---|---|---|
| Protein | Clone Designation | Status | (Nucle-otide) | (Amino Acid) |
| | w1m96.pk038.j7 | | | |
| | wlmk1.pk0019.g12 | | | |
| | wr1.pk0147.e6 | | | |
| | wr1.pk149.h5 | | | |
| | wr1.pk172.b11 | | | |
| | wre1n.pk0031.h7 | | | |
| | wre1n.pk0095.h11 | | | |
| | wre1n.pk0096.f1 | | | |
| | wre1n.pk0142.e3 | | | |
| CCOMT (Wheat) | w1m96.pk037.m21:fis | CGS | 45 | 46 |
| CCOMT (Wheat) | Contig of: | Contig | 47 | 48 |
| | wdk2c.pk007.19 | | | |
| | wkm2c.pk005.b15 | | | |

The Sequence Listing contains the one letter code for nucleotide sequence characters and the three letter codes for amino acids as defined in conformity with the IUPAC-IUBMB standards described in *Nucleic Acids Res.* 13:3021–3030 (1985) and in the *Biochemical J.* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, a "polynucleotide" is a nucleotide sequence such as a nucleic acid fragment. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. An isolated polynucleotide of the present invention may include at least one of 60 contiguous nucleotides, preferably at least one of 40 contiguous nucleotides, most preferably one of at least 30 contiguous nucleotides, of the nucleic acid sequence of the SEQ ID NOs: 1, 5, 7, 9, 13, 15, 19, 23, 25, 27, 29, 31, 33, 35, 39, 41, 43, 45, and 47.

As used herein, "contig" refers to a nucleotide sequence that is assembled from two or more constituent nucleotide sequences that share common or overlapping regions of sequence homology. For example, the nucleotide sequences of two or more nucleic acid fragments can be compared and aligned in order to identify common or overlapping sequences. Where common or overlapping sequences exist between two or more nucleic acid fragments, the sequences (and thus their corresponding nucleic acid fragments) can be assembled into a single contiguous nucleotide sequence.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to nucleic acid fragments wherein changes in one or more nucleotide bases does not affect the ability of the nucleic acid fragment to mediate alteration of gene expression by gene silencing through for example antisense or co-suppression technology. "Substantially similar" also refers to modifications of the nucleic acid fragments of the instant invention such as deletion or insertion of one or more nucleotides that do not substantially affect the functional properties of the resulting transcript vis-a-vis the ability to mediate gene silencing or alteration of the functional properties of the resulting protein molecule. It is therefore understood that the invention encompasses more than the specific exemplary nucleotide or amino acid sequences and includes functional equivalents thereof.

Substantially similar nucleic acid fragments may be selected by screening nucleic acid fragments representing subfragments or modifications of the nucleic acid fragments of the instant invention, wherein one or more nucleotides are substituted, deleted and/or inserted, for their ability to affect the level of the polypeptide encoded by the unmodified nucleic acid fragment in a plant or plant cell. For example, a substantially similar nucleic acid fragment representing at least one of 30 contiguous nucleotides derived from the instant nucleic acid fragment can be constructed and introduced into a plant or plant cell. The level of the polypeptide encoded by the unmodified nucleic acid fragment present in a plant or plant cell exposed to the substantially similar nucleic fragment can then be compared to the level of the polypeptide in a plant or plant cell that is not exposed to the substantially similar nucleic acid fragment.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a nucleic acid fragment which result in the production of a chemically equivalent amino acid at a given site, but do not effect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. Consequently, an isolated polynucleotide comprising a nucleotide sequence of at least one of 60 (preferably at least one of 40, most preferably at least one of 30) contiguous nucleotides derived from a nucleotide sequence selected from the group consisting of SEQ ID NOs:1, 5, 7, 9, 13, 15, 19, 23, 25, 27, 29, 31, 33, 35, 39, 41, 43, 45, and 47 and the complement of such nucleotide sequences may be used in methods of selecting an isolated polynucleotide that affects the expression of a polypeptide in a plant cell. A method of selecting an isolated polynucleotide that affects the level of expression of a polypeptide, such as Caffeoyl-CoA O-Methyltransferase in a host cell (eukaryotic, such as plant or yeast, prokaryotic such as bacterial, or viral) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (Hames and Higgins, Eds. (1985) Nucleic Acid Hybridisation, IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms. Post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C.

Substantially similar nucleic acid fragments of the instant invention may also be characterized by the percent identity of the amino acid sequences that they encode to the amino acid sequences disclosed herein, as determined by algorithms commonly employed by those skilled in this art. Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are at least about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least about 25 amino acids, more preferably at least about 50 amino acids, preferably at least about 100 amino acids, more preferably at least about 150 amino acids, still more preferably at least about 200 amino acids, and most preferably at least about 250 amino acids. Sequence alignments and percent identity calculations were performed using the Megalign program of the LASER-GENE bioinformatics computing suite (DNASTAR Inc., Madison, Wis.). Multiple alignment of the sequences was performed using the Clustal method of alignment (Higgins and Sharp (1989) CABIOS. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST (Basic Local Alignment Search Tool; Altschul et al. (1993) *J. Mol. Biol.* 215:403–410; see also www.ncbi.nlm.nih.gov/BLAST/). In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12 or more nucleotides may be used as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The instant specification teaches amino acid and nucleotide sequences encoding polypeptides that comprise one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without effecting the amino acid sequence of an encoded polypeptide. Accordingly, the instant invention relates to any nucleic acid fragment comprising a nucleotide sequence that encodes all or a substantial portion of the amino acid sequences set forth herein. The skilled artisan is well aware of the "codon-bias" exhibited by a specific host cell in usage of nucleotide codons to specify a given amino acid. Therefore, when synthesizing a nucleic acid fragment for improved expression in a host cell, it is desirable to design the nucleic acid fragment such that its frequency of codon usage approaches the frequency of preferred codon usage of the host cell.

"Synthetic nucleic acid fragments" can be assembled from oligonucleotide building blocks that are chemically synthesized using procedures known to those skilled in the art. These building blocks are ligated and annealed to form larger nucleic acid fragments which may then be enzymatically assembled to construct the entire desired nucleic acid fragment. "Chemically synthesized", as related to nucleic acid fragment, means that the component nucleotides were assembled in vitro. Manual chemical synthesis of nucleic acid fragments may be accomplished using well established procedures, or automated chemical synthesis can be performed using one of a number of commercially available machines. Accordingly, the nucleic acid fragments can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a nucleotide sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a nucleotide sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a nucleotide sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic nucleotide segments. It is understood by those skilled in the art that different promoters may direct the expression of a gene in different tissues or cell types, or at different stages of development, or in response to different environmental conditions. Promoters which cause a nucleic acid fragment to be expressed in most cell types at most times are commonly referred to as "constitutive promoters". New promoters of various types useful in plant cells are constantly being discovered; numerous examples may be found in the compilation by Okamuro and Goldberg (1989) *Biochemistry of Plants* 15:1–82. It is further recognized that since in most cases the exact boundaries of regulatory sequences have not been completely defined, nucleic acid fragments of different lengths may have identical promoter activity.

The "translation leader sequence" refers to a nucleotide sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner and Foster (1995) *Mol. Biotechnol.* 3:225–236).

The "3' non-coding sequences" refer to nucleotide sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al. (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into polypeptide by the cell. "cDNA" refers to a double-stranded DNA that is complementary to and derived from mRNA. "Sense" RNA refers to an RNA transcript that includes the mRNA and so can be translated into a polypeptide by the cell. "Antisense RNA" refers to an RNA transcript that is complementary to all or part of a target primary transcript or mRNA and that blocks the expression of a target gene (see U.S. Pat. No. 5,107,065, incorporated herein by reference). The complementarity of an antisense RNA may be with any part of the specific nucleotide sequence, i.e., at the 5' non-coding sequence, 3' non-coding sequence, introns, or the coding sequence. "Functional RNA" refers to sense RNA, antisense RNA, ribozyme RNA, or other RNA that may not be translated but yet has an effect on cellular processes.

The term "operably linked" refers to the association of two or more nucleic acid fragments on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Underexpression" refers to the production of a gene product in transgenic organisms at levels below that of levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product (s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook et al. *Molecular Cloning: A Laboratory Manual*; Cold Spring Harbor Laboratory Press: Cold Spring Harbor, 1989 hereinafter "Maniatis").

Nucleic acid fragments encoding at least a portion of several caffeoyl-CoA O-methyltransferase have been isolated and identified by comparison of random plant cDNA sequences to public databases containing nucleotide and protein sequences using the BLAST algorithms well known to those skilled in the art. The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other caffeoyl-CoA O-methyltransferase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al. (1988) *Proc. Natl. Acad. Sci. USA* 85:8998–9002) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al. (1989) *Proc. Natl. Acad. Sci. USA* 86:5673–5677; Loh et al. (1989) *Science* 243:217–220). Products generated by the 3' and 5' RACE procedures can be combined to generate full-length cDNAs (Frohman and Martin (1989) *Techniques* 1:165). Consequently, a polynucleotide comprising a nucleotide sequence of at least one of 60 (preferably one of at least 40, most preferably one of at least 30) contiguous nucleotides derived from a nucleotide sequence selected from the group consisting of SEQ ID NOs:1, 5, 7, 9, 13, 15, 19, 23, 25, 27, 29, 31, 33, 35, 39, 41, 43, 45, and 47 and the complement of such nucleotide sequences may be used in such methods to obtain a nucleic acid fragment encoding a substantial portion of an amino acid sequence of a polypeptide. The present invention relates to a method of obtaining a nucleic acid fragment encoding a substantial portion of a polypeptide of a gene (such as caffeoyl-CoA O-methyltransferase) preferably a substantial portion of a plant polypeptide of a gene, comprising the steps of: synthesizing an oligonucleotide primer comprising a nucleotide sequence of at least one of 60 (preferably at least one of 40, most preferably at least one of 30) contiguous nucleotides derived from a nucleotide sequence selected from the group consisting of SEQ ID NOs:1, 5, 7, 9, 13, 15, 19, 23, 25, 27, 29, 31, 33, 35, 39, 41, 43, 45, and 47 and the complement of such nucleotide sequences; and amplifying a nucleic acid fragment (preferably a cDNA inserted in a cloning vector) using the oligonucleotide primer. The amplified nucleic acid fragment preferably will encode a portion of a polypeptide.

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner (1984) *Adv. Immunol.* 36:1–34; Maniatis).

The nucleic acid fragments of the instant invention may be used to create transgenic plants in which the disclosed polypeptides are present at higher or lower levels than normal or in cell types or developmental stages in which they are not normally found. This would have the effect of altering the level of lignin production in those cells.

Overexpression of the proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then be constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al. (1985) *EMBO J*. 4:2411–2418; De Almeida et al. (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant polypeptides to different cellular compartments, or to facilitate its secretion from the cell. It is thus envisioned that the chimeric gene described above may be further supplemented by altering the coding sequence to encode the instant polypeptides with appropriate intracellular targeting sequences such as transit sequences (Keegstra (1989) *Cell* 56:247–253), signal sequences or sequences encoding endoplasmic reticulum localization (Chrispeels (1991) *Ann. Rev. Plant Phys. Plant Mol. Biol.* 42:21–53), or nuclear localization signals (Raikhel (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding the instant polypeptides in plants for some applications. In order to accomplish this, a chimeric gene designed for co-suppression of the instant polypeptide can be constructed by linking a gene or gene fragment encoding that polypeptide to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

Molecular genetic solutions to the generation of plants with altered gene expression have a decided advantage over more traditional plant breeding approaches. Changes in plant phenotypes can be produced by specifically inhibiting expression of one or more genes by antisense inhibition or cosuppression (U.S. Pat. Nos. 5,190,931, 5,107,065 and 5,283,323). An antisense or cosuppression construct would act as a dominant negative regulator of gene activity. While conventional mutations can yield negative regulation of gene activity these effects are most likely recessive. The dominant negative regulation available with a transgenic approach may be advantageous from a breeding perspective. In addition, the ability to restrict the expression of specific phenotype to the reproductive tissues of the plant by the use of tissue specific promoters may confer agronomic advantages relative to conventional mutations which may have an effect in all tissues in which a mutant gene is ordinarily expressed.

The person skilled in the art will know that special considerations are associated with the use of antisense or cosuppression technologies in order to reduce expression of particular genes. For example, the proper level of expression of sense or antisense genes may require the use of different chimeric genes utilizing different regulatory elements known to the skilled artisan. Once transgenic plants are obtained by one of the methods described above, it will be necessary to screen individual transgenics for those that most effectively display the desired phenotype. Accordingly, the skilled artisan will develop methods for screening large numbers of transformants. The nature of these screens will generally be chosen on practical grounds, and is not an inherent part of the invention. For example, one can screen by looking for changes in gene expression by using antibodies specific for the protein encoded by the gene being suppressed, or one could establish assays that specifically measure enzyme activity. A preferred method will be one which allows large numbers of samples to be processed rapidly, since it will be expected that a large number of transformants will be negative for the desired phenotype.

The instant polypeptides (or portions thereof) may be produced in heterologous host cells, particularly in the cells of microbial hosts, and can be used to prepare antibodies to the these proteins by methods well known to those skilled in the art. The antibodies are useful for detecting the polypeptides of the instant invention in situ in cells or in vitro in cell extracts. Preferred heterologous host cells for production of the instant polypeptides are microbial hosts. Microbial expression systems and expression vectors containing regulatory sequences that direct high level expression of foreign proteins are well known to those skilled in the art. Any of these could be used to construct a chimeric gene for production of the instant polypeptides. This chimeric gene could then be introduced into appropriate microorganisms via transformation to provide high level expression of the encoded caffeoyl-CoA O-methyltransferase. An example of a vector for high level expression of the instant polypeptides in a bacterial host is provided (Example 6).

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et al. (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein et al. (1980) *Am. J Hum. Genet.* 32:314–331).

The production and use of plant gene-derived probes for use in genetic mapping is described in Bernatzky and Tanksley (1986) *Plant Mol. Biol. Reporter* 4:37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel et al. In: *Nonmammalian Genomic Analysis: A Practical Guide*, Academic press 1996, pp. 319–346, and references cited therein).

In another embodiment, nucleic acid probes derived from the instant nucleic acid sequences may be used in direct fluorescence in situ hybridization (FISH) mapping (Trask (1991) *Trends Genet*. 7:149–154). Although current methods of FISH mapping favor use of large clones (several to several hundred KB; see Laan et al. (1995) *Genome Res*. 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian (1989) *J. Lab. Clin. Med*. 11:95–96), polymorphism of PCR-amplified fragments (CAPS; Sheffield et al. (1993) *Genomics* 16:325–332), allele-specific ligation (Landegren et al. (1988) *Science* 241:1077–1080), nucleotide extension reactions (Sokolov (1990) *Nucleic Acid Res*. 18:3671), Radiation Hybrid Mapping (Walter et al. (1997) *Nat. Genet*. 7:22–28) and Happy Mapping (Dear and Cook (1989) *Nucleic Acid Res*. 17:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer (1989) *Proc. Natl. Acad. Sci USA* 86:9402–9406; Koes et al. (1995) *Proc. Natl. Acad. Sci USA* 92:8149–8153; Bensen et al. (1995) *Plant Cell* 7:75–84). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the instant polypeptide. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding the instant polypeptide can be identified and obtained. This mutant plant can then be used to determine or confirm the natural function of the instant polypeptides disclosed herein.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cbn10 | Corn (*Zea mays L*) Developing Kernel (Embryo and Endosperm); 10 Days After Pollination | cbn10.pk0030.a9<br>cbn10.pk0058.e4 |
| cen3n | Corn (*Zea mays L*) Endosperm 20 Days After Pollination* | cen3n.pk0060.b10<br>cen13n.pk0125.b2 |
| cepe7 | Corn (*Zea mays L*) 7 Day Old Epicotyl From Etiolated Seedling | cepe7.pk0012.c4<br>cepe7.pk0028.h4 |
| cho1c | Corn (*Zea mays L*, Alexho Synthetic High Oil) Embryo 20 Days After Pollination | cho1c.pk003.a13 |
| cpk1c | Corn (*Zea mays L*) Pooled BMS Treated With Chemicals Related to Membrane Traffic** | cpk1c.pk001.1121 |
| cr1n | Corn (*Zea Mays L*) Root From 7 Day Old Seedlings* | cr1n.pk0002.c6<br>cr1n.pk0063.c9<br>cr1n.pk0098.f2<br>cr1n.pk0153.b2<br>cr1n.pk0158.c3<br>cr1n.pk0168.h5<br>cr1n.pk0170.d8 |

TABLE 2-continued cDNA Libraries from Corn, Rice, Soybean, and Wheat

| Library | Tissue | Clone |
|---|---|---|
| | | cr1n.pk0171.e4 |
| | | cr1n.pk0179.e10 |
| cr1s | Corn *(Zea Mays L)* Root From 7 Day Old Etiolated Seedling | cr1s.pk014.c4 |
| csi1n | Corn *(Zea Mays L)* Silk* | csi1n.pk0020.c11 |
| cta1n | Corn *(Zea Mays L)* Tassel* | cta1n.pk0009.e4 |
| r10n | Rice *(Oryza sativa)* 15 Day Old Leaf* | r10n.pk082.i11 |
| | | r10n.pk085.k12 |
| | | r10n.pk091.11 |
| r1r24 | Rice *(Oryza sativa)* Leaf 15 Days After Germination, 24 Hours After Infection of Strain *Magaporthe grisea* 4360-R-62 (AVR2-YAMO); Resistant | r1r24.pk0093.a3 |
| r1r48 | Resistant Rice *(Oryza sativa)* Leaf 15 Days After Germination, 48 Hours After Infection of Strain *Magaporthe grisea* 4360-R-62 (AVR2-YAMO) | r1r48.pk0039.b7 |
| r1s24 | Susceptible Rice *(Oryza sativa)* Leaf 15 Days After Germination, 24 Hours After Infection of Strain *Magaporthe grisea* 4360-R-67 (AVR2-YAMO) | r1s24.pk0021.b11 |
| rr1 | Rice *(Oryza sativa)* Root of Two Week Old Developing Seedling | rr1.pk0043.g9 |
| | | rr1.pk0047.g8 |
| rs11n | Rice *(Oryza sativa)* 15-Day-Old Seedling* | rs11n.pk001.o7 |
| sdp2c | Soybean *(Glycine max L)* Developing Pod (6–7 mm) | sdp2c.pk002.j20 |
| | | sdp2c.pk014.j8 |
| sdp3c | Soybean *(Glycine max L)* Developing Pod (8–9 mm) | sdp3c.pk011.m2 |
| sf11 | Soybean *(Glycine max L)* Immature Flower | sf11.pk0006.a7 |
| | | sf11.pk135.h3 |
| sf11n1 | Soybean Immature Flower* | sf11n1.pk001.a9 |
| sgc3c | Soybean *(Glycine max L)* Cotyledon 14–21 Days After Germination (Starting to Turn Yellow) | sgc3c.pk001.17 |
| sgs4c | Soybean *(Glycine max L)* Seed 2 Days After Germination | sgs4c.pk003.d5 |
| s12 | Soybean *(Glycine max L)* Two-Week-Old Developing Seedling Treated With 2.5 ppm chlorimuron | s12.pk0046.g8 |
| | | s12.pk0088.g6 |
| | | s12.pk0100.a8 |
| | | s12.pk122.115 |
| s1s1c | Soybean *(Glycine max,* variety S1990) Infected With *Sclerotinia sclerotiorum* Mycelium | s1s1c.pk008.g24 |
| | | s1s1c.pk009.j22 |
| sr1 | Soybean *(Glycine max L)* Root | sr1.pk0077.h10 |
| src2c | Soybean *(Glycine max L)* 8 Day Old Root Infected With Eggs of Cyst Nematode *(Heteroderea glycensis)* (Race 1) for 4 Days | src2c.pk001.o12 |
| | | src2c.pk002.g14 |
| | | src2c.pk003.b20 |
| | | src2c.pk003.e4 |
| | | src2c.pk010.f17 |
| sre | Soybean *(Glycine max L)* Root Elongation Zone 4 to 5 Days After Germination | sre.pk0002.c9 |
| | | sre.pk0002.f9 |
| | | sre.pk0044.c3 |
| wdk2c | Wheat *(Triticum aestivum L)* Developing Kernel, 7 Days After Anthesis | wdk2c.pk006.k18 |
| | | wdk2c.pk007.19 |
| wkm2c | Wheat *(Triticum aestivum L)* Kernel Malted 175 Hours at 4° C. | wkm2c.pk005.b15 |
| wl1n | Wheat *(Triticum aestivum L)* Leaf From 7 Day Old Seedling Light Grown* | wl1n.pk0010.f2 |
| | | wl1n.pk0140.h9 |
| | | wl1n.pk0141.a9 |
| w1e1n | Wheat *(Triticum aestivum L)* Leaf From 7 Day Old Etiolated Seedling* | w1e1n.pk0014.d12 |
| | | w1e1n.pk0035.g8 |
| | | w1e1n.pk0083.e5 |
| w1k1 | Wheat *(Triticum aestivum L)* Seedling 1 Hour After Treatment With Herbicide KQ926*** | w1k1.pk0006.b2 |
| | | w1k1.pk0020.g6 |
| w1m96 | Wheat *(Triticum aestivum L)* Seedling 96 Hours After Inoculation With *Erysiphe graminis f sp tritici* | w1m96.pk033.j2 |
| | | w1m96.pk036.e8 |
| | | w1m96.pk037.m21 |
| | | w1m96.pk038.j7 |
| w1mk1 | Wheat *(Triticum aestivum L)* Seedling 1 Hour After Inoculation With *Erysiphe graminis f sp tritici* and Treatment With Herbicide KQ926*** | w1mk1.pk0016.g9 |
| | | w1mk1.pk0017.e5 |
| | | w1mk1.pk0019.g12 |
| wr1 | Wheat *(Triticum aestivum L)* Root From 7 Day Old Seedling Light Grown | wr1.pk0147.e6 |
| | | wr1.pk149.h5 |
| | | wr1.pk172.b11 |
| wre1n | Wheat *(Triticum aestivum L)* Root From 7 Day Old Etiolated Seedling* | wre1n pk0031.h7 |
| | | wre1n.pk0062.h9 |
| | | wre1n.pk0095.h11 |
| | | wre1n.pk0096.f1 |

TABLE 2-continued cDNA Libraries from Corn, Rice, Soybean, and Wheat

| Library | Tissue | Clone |
|---|---|---|
| | | wre1n.pk0112.d4 |
| | | wre1n.pk0142.e3 |

*These libraries were normalized essentially as described in U.S. Pat. No. 5,482,845, incorporated herein by reference.
**Membrane traffic chemicals used include tunicamycin, brefeldin A and cytocholasin B, all of which are commercially available from Calbiochem-Novabiochem Corp. (1-800-628-8470).
***Application of 6-iodo-2-propoxy-3-propyl-4(3H)-quinazolinone; synthesis and methods of using this compound are described in USSN 08/545,827, incorporated herein by reference.

cDNA libraries may be prepared by any one of many methods available. For example, the cDNAs may be introduced into plasmid vectors by first preparing the cDNA libraries in Uni-ZAP™ XR vectors according to the manufacturer's protocol (Stratagene Cloning Systems, La Jolla, Calif.). The Uni-ZAP™ XR libraries are converted into plasmid libraries according to the protocol provided by Stratagene. Upon conversion, cDNA inserts will be contained in the plasmid vector pBluescript. In addition, the cDNAs may be introduced directly into precut Bluescript II SK(+) vectors (Stratagene) using T4 DNA ligase (New England Biolabs), followed by transfection into DH10B cells according to the manufacturer's protocol (GIBCO BRL Products). Once the cDNA inserts are in plasmid vectors, plasmid DNAs are prepared from randomly picked bacterial colonies containing recombinant pBluescript plasmids, or the insert cDNA sequences are amplified via polymerase chain reaction using primers specific for vector sequences flanking the inserted cDNA sequences. Amplified insert DNAs or plasmid DNAs are sequenced in dye-primer sequencing reactions to generate partial cDNA sequences (expressed sequence tags or "ESTs"; see Adams et al., (1991) *Science* 252:1651–1656). The resulting ESTs are analyzed using a Perkin Elmer Model 377 fluorescent sequencer.

Example 2

Identification of cDNA Clones cDNA clones encoding caffeoyl-CoA O-methyltransferases were identified by conducting BLAST (Basic Local Alignment Search Tool; Altschul et al. (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish and States (1993) *Nat. Genet.* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Caffeoyl-CoA O-Methyltransferase

The BLASTX search using the EST sequences from clones cr1n.pk0002.c6, cr1n.pk0168.h5, cr1n.pk0063.c9, cr1n.pk0179.e10, cr1n.pk0153.b2, r10n.pk085.k12, r1s24.pk0021.b11, r10n.pk091.11, wlm96pk036.e8, wlmk1.pk0017.e5, wlk1.pk0020.g6, wdk2c.pk006.k18 and wlmk1.pk0016.g9 revealed similarity of the proteins encoded by the cDNAs to caffeoyl-CoA O-methyltransferase from *Populus balsamifera* (NCBI Identifier No. gi2960356). The BLASTX search using the EST sequences from clones sre.pk0044.c3, sre.pk0002.f9, sre.pk0002.c9, sdp3c.pk011.m2, sdp2c.pk002.j20 and src2c.pk002.g14 revealed similarity of the proteins encoded by the cDNAs to caffeoyl-CoA O-methyltransferase from *Medicago sativa* (NCBI Identifier No. gi684942). The BLASTX search using the EST sequences from clones wl1n.pk0141.a9, wl1n.pk0140.h9, wl1n.pk0010.f2, wlm96.pk033.j2, wre1n.pk0112.d4, wlk1.pk0006.b2, wle1n.pk0035.g8, wre1n.pk0062.h9 and wle1n.pk0083.e5 revealed similarity of the proteins encoded by the cDNAs to caffeoyl-CoA O-methyltransferase from *Nicotina tabacum* (NCBI Identifier No. gi2511737).

In the process of comparing the ESTs it was found that the following groups of clones had overlapping regions of homology: (i) clones cr1n.pk0002.c6, cr1n.pk0168.h5, cr1n.pk0063.c9, cr1n.pk0179.e10 and cr1n.pk0153.b2; (ii) clones r10n.pk085.k12, r1s24.pk0021.b11 and r10n.pk091.11; (iii) clones wlm96.pk036.e8, wlmk1.pk0017.e5, wlk1.pk0020.g6, wdk2c.pk006.k18 and wlmk1.pk0016.g9; (iv) clones sre.pk0044.c3, sre.pk0002.f9, sre.pk0002.c9, sdp3c.pk01.m2, sdp2c.pk002.j20 and src2c.pk002.g14; and (v) clones wl1n.pk0141.a9, wl1n.pk0140.h9, wl1n.pk0010.f2, wlm96.pk033.j2, wre1n.pk0112.d4, wlk1.pk0006.b2, wle1n.pk0035.g8, wre1n.pk0062.h9 and wle1n.pk0083.e5. Using these homologies, it was possible to align the ESTs and assemble individual contigs (a contig is an assemblage of overlapping nucleic acid sequences to form one contiguous nucleotide sequence). The individual sequences were assembled into contiguous nucleotide sequences encoding unique corn, rice, soybean and wheat caffeoyl-CoA O-methyltransferase proteins. The BLAST results for each of the contigs are shown in Table 3:

TABLE 3

BLAST Results for Clones Encoding Polypeptides Homologous to Caffeoyl-CoA O-Methyltransferase

| Clone | BLAST pLog Score (NCBI Identifier No.) |
|---|---|
| Contig composed of: | 132.00 (gi2960356) |
| cr1n.pk0002.c6 | |
| cr1n.pk0168.h5 | |
| cr1n.pk0063.c9 | |
| cr1n.pk0179.e10 | |
| cr1n.pk0153.b2 | |
| Contig composed of: | 57.40 (gi2960356) |
| r10n.pk085.k12 | |
| r1s24.pk0021.b11 | |
| r10n.pk091.11 | |
| Contig composed of: | 158.00 (gi684942) |
| sre.pk0044.c3 | |
| sre.pk0002.f9 | |
| sre.pk0002.c9 | |
| sdp3c.pk011.m2 | |
| sdp2c.pk002.j20 | |
| src2c.pk002.g14 | |
| Contig composed of: | 124.00 (gi2511737) |
| w11n.pk0141.a9 | |
| w11n.pk0140.h9 | |
| w11n.pk0010.f2 | |
| w1m96.pk033j2 | |
| wre1n.pk0112.d4 | |
| w1k1.pk0006.b2 | |
| w1e1n.pk0035.g8 | |
| wre1n.pk0062.h9 | |
| w1e1n.pk0083.e5 | |
| Contig composed of: | 52.70 (gi2960356) |
| w1m96.pk036.e8 | |
| w1mk1.pk0017.e5 | |
| w1k1.pk0020.g6 | |
| wdk2c.pk006.k18 | |
| w1mk1.pk0016.g9 | |

The sequence of the corn contig assembled from clones cr1n.pk0002.c6, cr1n.pk0168.h5, cr1n.pk0063.c9, cr1n.pk0179.e10 and cr1n.pk0153.b2 encoding a caffeoyl-CoA O-methyltransferase protein (less five amino acids at the C-terminal end of the polypeptide) is shown in SEQ ID NO:1; the deduced amino acid sequence of this contig is shown in SEQ ID NO:2. The sequence of the rice contig assembled from clones r10n.pk085.k12, r1s24.pk0021.b11 and r10n.pk091.11 is shown in SEQ ID NO:9; the deduced amino acid sequence of this contig is shown in SEQ ID NO:10. The sequence of the soybean contig assembled from clones sre.pk0044.c3, sre.pk0002.f9, sre.pk0002.c9, sdp3c.pk011.m2, sdp2c.pk002.j20 and src2c.pk002.g14 encoding the entire caffeoyl-CoA O-methyltransferase protein is shown in SEQ ID NO:17; the deduced amino acid sequence of this contig is shown in SEQ ID NO:18. SEQ ID NO:18 is very similar to the caffeoyl-CoA O-methyltransferase amino acid sequence from *Medicago sativa* subsp. *sativa* (Inoue et al. (1998) *Plant Physiol.* 117:761–770; NCBI General Identification No. 684942). The sequence of the wheat contig assembled from clones w11n.pk41.a9, w11n.pk0140.h9, w11n.pk0010.f2, w1m96.pk033.j2, wre1n.pk0112.d4, w1k1.pk0006.b2, w1e1n.pk0035.g8, wre1n.pk0062.h9 and w1e1n.pk0083.e5 encoding the entire caffeoyl-CoA O-methyltransferase protein is shown in SEQ ID NO:35; the deduced amino acid sequence of this contig is shown in SEQ ID NO:36. The sequence of the wheat contig assembled from clones w1m96.pk036.e8, w1mk1.pk0017.e5, w1k1.pk0020.g6, wdk2c.pk006.k18 and w1mk1.pk0016.g9 is shown in SEQ ID NO:39; the deduced amino acid sequence of this contig is shown in SEQ ID NO:40.

A blastn/dbest search of the public database using the corn contig (SEQ ID NO:1) revealed several corn EST sequences (NCBI Identifier No. gi1366552) in the public domain that had significant identity to the instant corn contig. These EST sequences do not represent a full length cDNA encoding a caffeoyl-CoA O-methyltransferase protein, and represent less than 27% of a caffeoyl-CoA O-methyltransferase cDNA sequence.

The BLASTX search using the EST sequences from clones cbn10.pk0058.e4, cr1n.pk0170.d8, cta1n.pk0009.e4, cbn10.pk0030.a9, cr1n.pk0098.f2, cepe7.pk0012.c4, cr1s.pk014.c4, cr1n.pk0158.c3 and cpk1c.pk001.h21 revealed similarity of the proteins encoded by the cDNAs to caffeoyl-CoA O-methyltransferase from *Nicotiana tabacum* (NCBI Identifier No. gi 1679853). The BLASTX search using the EST sequences from clones rr1.pk0043.g9, rr1.pk0047.g8, rs11n.pk001.o7, r1r24.pk0093.a3, sgs4c.pk003.d5, src2c.pk003.e4, sfl1.pk135.h3, sdp2c.pk014.j8, sr1.pk0077.h10, w1m96.pk037.m21, w1mk1.pk0019.g12, w1m96.pk038.j7, wre1n.pk0096.f1, wr1.pk172.b11, wre1n.pk0031.h7, wr1.pk0147.e6, w1e1n.pk0014.d12, wre1n.pk0142.e3, wre1n.pk0095.h11 and wr1.pk149.h5 revealed similarity of the proteins encoded by the cDNAs to caffeoyl-CoA O-methyltransferase from *Populus balsamifera* (NCBI Identifier No. gi 2960356).

In the process of comparing the ESTs it was found that the following groups of clones had overlapping regions of homology: (i) clones cbn10.pk0058.e4, cr1n.pk0170.d8, cta1n.pk0009.e4, cbn10.pk0030.a9, cr1n.pk0098.f2, cepe7.pk0012.c4, cr1s.pk014.c4, cr1n.pk0158.c3 and cpk1c.pk001.h21; (ii) clones rr1.pk0043.g9, rr1.pk0047.g8, rs11n.pk001.o7, r1r24.pk0093.a3; (iii) clones sgs4c.pk003.d5, src2c.pk003.e4, sfl1.pk135.h3, sdp2c.pk014.j8, sr1.pk0077.h10; and (iv) clones w1m96.pk037.m21, w1mk1.pk0019.g12, w1m96.pk038.j7, wre1n.pk0096.f1, wr1.pk172.b11, wre1n.pk0031.h7, wr1.pk0147.e6, w1e1n.pk0014.d12, wre1n.pk0142.e3, wre1n.pk0095.h11 and wr1.pk149.h5.

Using this homology it was possible to align the ESTs and assemble individual contigs. The individual sequences were assembled into contiguous nucleotide sequences encoding unique caffeoyl-CoA O-methyltransferase proteins. The BLAST results for each of the contigs are shown in Table 4:

TABLE 4

BLAST Results for Clones Encoding Polypeptides Homologous to Caffeoyl-CoA O-Methyltransferase

| Clone | BLAST pLog Score (NCBI Identifier No.) |
|---|---|
| Contig composed of: | 92.00 (gi1679853) |
| cbn10.pk0058.e4 | |
| cr1n.pk0170.d8 | |
| cta1n.pk0009.e4 | |
| cbn10.pk0030.a9 | |
| cr1n.pk0098.f2 | |
| cepe7.pk0012.c4 | |
| cr1s.pk014.c4 | |
| cr1n.pk0158.c3 | |
| cpk1c.pk001.h21 | |
| Contig composed of: | 82.52 (gi2960356) |
| rr1.pk0043.g9 | |
| rr1.pk0047.g8 | |
| rs11n.pk001.o7 | |
| r1r24.pk0093.a3 | |
| Contig composed of: | 115.00 (gi2960356) |
| sgs4c.pk003.d5 | |
| src2c.pk003.e4 | |

TABLE 4-continued

BLAST Results for Clones Encoding Polypeptides Homologous to Caffeoyl-CoA O-Methyltransferase

| Clone | BLAST pLog Score (NCBI Identifier No.) |
| --- | --- |
| sfl1.pk135.h3 | |
| sdp2c.pk014.j8 | |
| sr1.pk0077.h10 | |
| Contig composed of: | 89.04 (gi2960356) |
| wlm96.pk037.m21 | |
| wlmkl.pk0019.g12 | |
| wlm96.pk038.j7 | |
| wreln.pk0096.f1 | |
| wrl.pk172.b11 | |
| wreln.pk0031.h7 | |
| wrl.pk0147.e6 | |
| wle1n.pk0014.d12 | |
| wre1n.pk0142.e3 | |
| wre1n.pk0095.h11 | |
| wrl.k149.h5 | |

The sequence of the corn contig composed of clones cbn10.pk0058.e4, cr1n.pk0170.d8, cta1n.pk0009.e4, cbn10.pk0030.a9, cr1n.pk0098.f2, cepe7.pk0012.c4, cr1s.pk014.c4, cr1n.pk0158.c3 and cpk1c.pk001.h21 encoding the entire caffeoyl-CoA O-methyltransferase protein is shown in SEQ ID NO:5; the deduced amino acid sequence of this contig is shown in SEQ ID NO:6. The sequence of the rice contig composed of clones rr1.pk0043.g9, rr1.pk0047.g8, rsl1n.pk001.o7, rlr24.pk0093.a3 encoding the entire caffeoyl-CoA O-methyltransferase protein is shown in SEQ ID NO:13; the deduced amino acid sequence of this contig is shown in SEQ ID NO:14. The sequence of the soybean contig composed of clones sgs4c.pk003.d5, src2c.pk003.e4, sfl1.pk135.h3, sdp2c.pk014.j8, sr1.pk0077.h10 encoding the entire caffeoyl-CoA O-methyltransferase protein is shown in SEQ ID NO:19; the deduced amino acid sequence of this contig is shown in SEQ ID NO:20. The sequence of the wheat contig composed of clones wlm96.pk037.m21, wlmk1.pk009.g12, wlm96.pk038.j7, wre1n.pk0096.f1, wr1.pk172.b11, wre1n.pk0031.h7, wr1.pk0147.e6, wle1n.pk0014.d12, wre1n.pk0142.e3, wre1n.pk0095.h11 and wr1.pk149.h5 encoding the entire caffeoyl-CoA O-methyltransferase protein is shown in SEQ ID NO:43; the deduced amino acid sequence of this contig is shown in SEQ ID NO:44.

A blastn/dbest search of the public database using the rice contig (SEQ ID NO:13) revealed several rice EST sequences (NCBI Identifier No. gi 701308, gi 700492 and gi 701742) in the public domain that had significant identity to the instant rice contig. The EST sequences do not represent a full length cDNA encoding a caffeoyl-CoA O-methyltransferase protein and represent less than 46% of a caffeoyl-CoA O-methyltransferase cDNA sequence.

The BLASTX search using the EST sequences from clones cr1n.pk0171.e4, cho1c.pk003.a13, cen3n.pk0125.b2, csi1n.pk0020.c11, cen3n.pk0060.b10 and cepe7.pk0028.h4 revealed similarity of the proteins encoded by the cDNAs to caffeoyl-CoA o-methyltransferase from *Populus tremuloides* (NCBI Identifier No. gi 3023436). The BLASTX search using the EST sequences from clones src2c.pk003.b20, src2c.pk010.f17, src2c.pk001.o12 and s12.pk0100.a8 revealed similarity of the proteins encoded by the cDNAs to caffeoyl-CoA o-methyltransferase from *Medicago sativa* (NCBI Identifier No. gi 684942). BLASTX search using the EST sequences from clones wkm2c.pk005.b15 and wdk2c.pk007.19 revealed similarity of the proteins encoded by the cDNAs to caffeoyl-CoA o-methyltransferase from *Petroselinum crispum* (NCBI Identifier No. gi 115559).

In the process of comparing the ESTs it was found that the following groups of clones had overlapping regions of homology: (i) clones cr1n.pk0171.e4, cho1c.pk003.a13, cen3n.pk0125.b2, csi1n.pk0020.c11, cen3n.pk0060.b10 and cepe7.pk0028.h4; (ii) clones src2c.pk003.b20, src2c.pk010.f17, src2c.pk001.o12 and s12.pk0100.a8; and (iii) clones wkm2c.pk005.b15 and wdk2c.pk007.19.

Using this homology it was possible to align the ESTs and assemble individual contigs. The individual sequences were assembled into contiguous nucleotide sequences encoding unique caffeoyl-CoA O-methyltransferase proteins. The BLAST results for each of the contigs are shown in Table 5:

TABLE 5

BLAST Results for Clones Encoding Polypeptides Homologous to Caffeoyl-CoA O-Methyltransferase

| Clone | BLAST pLog Score (NCBI Identifier No.) |
| --- | --- |
| Contig composed of: | 87.40 (gi3023436) |
| crln.pk0171.e4 | |
| cho1c.pk003.a13 | |
| cen3n.pk0125.b2 | |
| csi1n.pk0020.c11 | |
| cen3n.pk0060.b10 | |
| cepe7.pk0028.h4 | |
| Contig composed of: | 135.00 (gi684942) |
| src2c.pk003.b20 | |
| src2c.pk010.f17 | |
| src2c.pk001.o12 | |
| sl2.pk0100.a8 | |
| Contig composed of: | 48.40 (gi115559) |
| wkm2c.pk005.b15 | |
| wdk2c.pk007.19 | |

The sequence of the corn contig composed of clones cr1n.pk0171.e4, cho1c.pk003.a13, cen3n.pk0125.b2, csi1n.pk0020.c11, cen3n.pk0060.b10 and cepe7.pk0028.h4 encoding the entire caffeoyl-CoA O-methyltransferase protein is shown in SEQ ID NO:7; the deduced amino acid sequence of this contig is shown in SEQ ID NO:8. The sequence of the soybean contig composed of clones src2c.pk003.b20, src2c.pk010.f17, src2c.pk001.o12 and sl2.pk0100.a8 encoding the entire caffeoyl-CoA O-methyltransferase protein is shown in SEQ ID NO:23; the deduced amino acid sequence of this contig is shown in SEQ ID NO:24. The sequence of the wheat contig composed of clones wkm2c.pk005.b15 and wdk2c.pk007.19 is shown in SEQ ID NO:47; the deduced amino acid sequence of this contig is shown in SEQ ID NO:48.

The BLASTX search using the EST sequences from clones sgc3c.pk001.17, sls1c.pk009j22, sl2.pk122.115, sl2.pk0046.g8, and sl2.pk0088.g6 revealed similarity proteins encoded by the cDNAs to caffeoyl-CoA O-methyltransferase from Stellaria longipes (NCBI Identifier No. gi 438897). In the process of comparing the ESTs it was found that clones sgc3c.pk001.17, sls1c.pk009.j22, sl2.pk122.115, sl2.pk0046.g8, and sl2.pk0088.g6 had overlapping regions of homology. Using this homology it was possible to align the ESTs and assemble a contig. The individual sequences were assembled into a contiguous nucleotide sequence encoding a unique soybean caffeoyl-CoA O-methyltransferase protein. The BLAST result is shown in Table 6:

TABLE 6

BLAST Results for Clones Encoding Polypeptides Homologous to Caffeoyl-CoA O-Methyltransferase

| Clone | BLAST pLog Score |
| --- | --- |
| Contig composed of:<br>sgc3c.pk001.17<br>sls1c.pk009.j22<br>sl2.pk122.11 5<br>sl2.pk0046.g8<br>sl2.pk0088.g6 | 87.30 |

The sequence of the soybean contig composd of clones sgc3c.pk001.17, sls1c.pk009j22, sl2.pk122.115, sl2.pk0046.g8, and sl2.pk0088.g6 encoding the entire caffeoyl-CoA O-methyltransferase protein is shown in SEQ ID NO:27; the deduced amino acid sequence of this contig is shown in SEQ ID NO:28.

The BLASTX search using the EST sequences from clones sfl1.pk0006.a7 and sfl1n1.pk001.a9 revealed similarity of the proteins encoded by the cDNAs to caffeoyl-CoA O-methyltransferase protein from *Nicotiana tabacum* (NCBI Identifier No. gi1679853). In the process of comparing the ESTs it was found that clones sfl1.pk0006.a7 and sfl1n1.pk001.a9 had overlapping regions of homology. Using this homology it was possible to align the ESTs and assemble a contig. The individual sequences were assembled into a contiguous nucleotide sequence encoding a unique soybean protein. The BLAST result is shown in Table 7:

TABLE 7

BLAST Results for Clones Encoding Polypeptides Homologous to Caffeoyl-CoA O-Methyltransferase Protein

| Clone | BLAST pLog Score |
| --- | --- |
| Contig composed of<br>sfl1.pk0006.a7<br>sfl1n1.pk001.a9 | 46.17 |

The sequence of the soybean contig composed of clones sfl1.pk0006.a7 and sfl1n1.pk001.a9 encoding an almost entire caffeoyl-CoA O-methyltransferase protein, with only a few amino acids absent from the N-terminal end, is shown in SEQ ID NO:29; the deduced amino acid sequence of this contig is shown in SEQ ID NO:30.

The BLASTX search using the EST sequence from clone sls1c.pk008.g24 revealed similarity of the protein encoded by the cDNA to caffeoyl-CoA O-methyltransferase protein from *Populus kitakamiensis* (NCBI Identifier No. gi 3023432). The BLAST result is shown in Table 8:

TABLE 8

BLAST Results for Clone Encoding Polypeptide Homologous to Caffeoyl-CoA O-Methyltransferase Protein

| Clone | BLAST pLog Score |
| --- | --- |
| sls1c.pk008.g24 | 43.30 |

The sequence of a portion of the cDNA insert from clone sls1c.pk008.g24 is shown in SEQ ID NO:33; the deduced amino acid sequence of this cDNA is shown in SEQ ID NO:34.

The nucleotide sequence of the entire cDNA insert in corn clone cr1n.pk0002.c6 was determined and is set forth in SEQ ID NO:3; the deduced amino acid sequence derived from SEQ ID NO:3 is set forth in SEQ ID NO:4. Relative to SEQ ID NO:2, SEQ ID NO:4 identifies the unknown amino acid and supplies the C-terminal three amino acids, thus exemplifying the complete amino acid sequence of a caffeoyl-CoA O-methyltransferase. SEQ ID NO:4 is identical to a maize sequence in WO 9910498-A2, published Mar. 4, 1999. Similarly, the nucleotide sequence of the entire cDNA insert in rice clone r10n.pk085.k12 was determined and is set forth in SEQ ID NO:11; the deduced amino acid sequence derived from SEQ ID NO:11 is set forth in SEQ ID NO:12 and represents the complete amino acid sequence of a caffeoyl-CoA O-methyltransferase. SEQ ID NO:12 is identical to the sequence in the public database designated with an NCBI General Identification No. 5091498. The nucleotide sequence of the entire cDNA insert in wheat clone wl1n.pk0141.a9 was determined and is set forth in SEQ ID NO:37; the deduced amino acid sequence derived from SEQ ID NO:37 is set forth in SEQ ID NO:38 and represents the complete amino acid sequence of a caffeoyl-CoA O-methyltransferase. SEQ ID NO:38 is virtually identical to a caffeoyl-CoA O-methyltransferase sequence from *Zea mays* (Civardi et al. (1999) *Plant Physiol* 120:1206; NCBI General Identification No. 5101868). The nucleotide sequence of the entire cDNA insert in wheat clone w1m96.pk036.e8 was determined and is set forth in SEQ ID NO:41; the deduced amino acid sequence derived from SEQ ID NO:41 is set forth in SEQ ID NO:42 and represents the complete amino acid sequence of a caffeoyl-CoA O-methyltransferase.

The nucleotide sequence of the entire cDNA insert in corn clone cbn10.pk0058.e4 was determined and found identical to the sequence set forth in SEQ ID NO:5, thus confirming the utility of contig assembly in determining full-length nucleotide sequence. The nucleotide sequence of the entire cDNA insert in soybean clone sgs4c.pk003.d5 was determined and is set forth in SEQ ID NO:2 1; the deduced amino acid sequence derived from SEQ ID NO:21 is set forth in SEQ ID NO:22 and represents the complete amino acid sequence of a caffeoyl-CoA O-methyltransferase. SEQ ID NO:22 is 96.7% identical to SEQ ID NO:20 which was derived from a contig of which a portion of the sequence from soybean clone sgs4c.pk003.d5 was part. SEQ ID NO:21 is very similar to soybean ESTs in the public database (e.g., NCBI General Identification Nos. 6073074, 5752909, and 5753226). The nucleotide sequence of the entire cDNA insert in wheat clone w1m96.pk037.m21 was determined and is set forth in SEQ ID NO:45; the deduced amino acid sequence derived from SEQ ID NO:45 is set forth in SEQ ID NO:46 and represents the complete amino acid sequence of a caffeoyl-CoA O-methyltransferase. SEQ ID NO:45 confirms the sequence of the contig set forth in SEQ ID NO:43, and SEQ ID NO:46 identifies the unknown amino acid at position 96 in SEQ ID NO:44 as an alanine.

The nucleotide sequence of the entire cDNA insert in soybean clone src2c.pk003.b20 was determined and is set forth in SEQ ID NO:25; the amino acid sequence derived from SEQ ID NO:25 is set forth in SEQ ID NO:26. SEQ ID NO:25 confirms the nucleotide sequence in SEQ ID NO:23, and SEQ ID NO:26 identifies the unknown amino acid at position 7 in SEQ ID NO:24 as glutamic acid.

The nucleotide sequence of the entire cDNA insert in soybean clone sfl1.pk0006.a7 was determined and is set forth in SEQ ID NO:31; the deduced amino acid sequence derived from SEQ ID NO:31 is set forth in SEQ ID NO:32.

The BLASTX search using the sequences from clones listed in Table 9 revealed similarity of the polypeptides encoded by the cDNAs to caffeoyl-CoA O-methyltransferase from *Zea mays* (NCBI General Identification No. 5101868), *Oryza sativa* (NCBI General Identification No. 5091498), *Populus tremuloides* (NCBI General Identification No. 3023436), *Populus balsamifera* subsp. *trichocarpa* (NCBI General Identification No. 2960356), *Medicago sativa* subsp. *sativa* (NCBI General Identification No. 684942), and *Arabidopsis thaliana* (NCBI General Identification No. 4539418). Shown in Table 9 are the BLAST results for individual ESTs ("EST", the sequences of the entire cDNA inserts comprising the indicated cDNA clones ("FIS"), contigs assembled from two or more ESTs ("Contig"), contigs assembled from an FIS and one or more ESTs ("Contig*"), or sequences encoding the entire protein derived from an FIS, a contig, or an FIS and PCR ("CGS"):

TABLE 9

BLAST Results for Sequences Encoding Polypeptides Homologous to Caffeoyl-CoA O-Methyltransferase (CCOMT)

| Clone | Status | BLAST Results Accession No. | pLog Score |
|---|---|---|---|
| cr1n.pk0002.c6 | CGS | 5101868 | 149.00 |
| rl0n.pk085.k12 | CGS | 5091498 | 150.00 |
| wl1n.pk0141.a9 | CGS | 5101868 | 149.00 |
| wlm96.pk036.e8 | CGS | 5091498 | 132.00 |
| gs4c.pk003.d5 | CGS | 3023436 | 104.00 |
| wlm96.pk037.m21 | CGS | 2960356 | 89.04 |
| Contig of rl0n.pk082.i11 rlr48.pk0039.b7 | Contig | 684942 | 23.70 |
| src2c.pk003.b20 | CGS | 684942 | 135.00 |
| sfl1.pk0006.a7 | CGS | 4539418 | 80.04 |

FIG. 1 presents an alignment of the amino acid sequences set forth in SEQ ID NOs:4, 6, 12, 14, 18, 22, 26, 28, 32, 38, 42, and 46 and the caffeoyl-CoA O-methyltransferase from *Zea mays* (NCBI General Identification No. 5101868) (SEQ ID NO:49) and *Populus tremuloides* (NCBI General Identification No. 3023436) (SEQ ID NO:50). The data in Table 10 represents a calculation of the percent identity of the amino acid sequences set forth in SEQ ID NOs:4, 6, 8, 12, 14, 18, 22, 26, 28, 32, 38, 42, and 46 and the caffeoyl-CoA O-methyltransferase sequence from *Zea mays* (NCBI General Identification No. 5101868) (SEQ ID NO:49) and *Populus tremuloides* (NCBI General Identification No. 3023436) (SEQ ID NO:50).

TABLE 10

Percent Identity of Amino Acid Sequences Deduced From the Nucleotide Sequences of cDNA Clones Encoding Polypeptides Homologous to Caffeoyl-CoA O-Methyltransferase

| | Percent Identity to NCBI General Identification No. | |
|---|---|---|
| SEQ ID NO. | 5101868 | 3023436 |
| 4 | 99.6 | 79.8 |
| 6 | 55.8 | 52.2 |
| 8 | 55.0 | 53.8 |
| 12 | 87.2 | 81.8 |
| 14 | 52.6 | 52.2 |
| 18 | 79.4 | 89.1 |
| 22 | 66.0 | 71.7 |
| 26 | 73.9 | 77.7 |
| 28 | 53.6 | 54.0 |
| 32 | 57.1 | 58.0 |
| 38 | 99.6 | 79.8 |

TABLE 10-continued

Percent Identity of Amino Acid Sequences Deduced From the Nucleotide Sequences of cDNA Clones Encoding Polypeptides Homologous to Caffeoyl-CoA O-Methyltransferase

| | Percent Identity to NCBI General Identification No. | |
|---|---|---|
| SEQ ID NO. | 5101868 | 3023436 |
| 42 | 84.9 | 80.6 |
| 46 | 56.0 | 53.8 |

Sequence alignments and percent identity calculations were performed using the Megalign program of the LASERGENE bioinformatics computing suite (DNASTAR Inc., Madison, Wis.). Multiple alignment of the sequences was performed using the Clustal method of alignment (Higgins and Sharp (1989) CABIOS. 5:151 –153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Sequence alignments and BLAST scores and probabilities indicate that the nucleic acid fragments comprising the instant cDNA clones encode all or substantial portions of a caffeoyl-CoA O-methyltransferase. The sequences disclosed herein represent the first corn, rice, soybean and wheat sequences encoding full-length caffeoyl-CoA O-methyltransferase.

Example 4

Expression of Chimeric Genes in Monocot Cells

A chimeric gene comprising a cDNA encoding the instant polypeptide in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML 103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (Epicurian Coli XL-1 Blue™; Stratagene). Bacterial transformants can be screened by restriction enzyme digestion of plasmid DNA and limited nucleotide sequence analysis using the dideoxy chain termination method (Sequenase# DNA Sequencing Kit; U.S. Biochemical). The resulting plasmid construct would comprise a chimeric gene encoding, in the 5' to 3' direction, the maize 27 kD zein promoter, a cDNA fragment encoding the instant polypeptide, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al. (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al. (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the glufosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al. (1990) *Bio/Technology* 8:833–839).

Example 5

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant polypeptides in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC 18 vector carrying the seed expression cassette.

Soybean embryos may then be transformed with the expression vector comprising sequences encoding the instant polypeptides. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Klein et al. (1987) *Nature* (London) 327:70–73, U.S. Pat. No. 4,945,050). A DuPont Biolistic™ PDS 1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli*; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the instant polypeptide and the phaseolin 3' region can be isolated as a restriction fragment. This fragment can then be inserted into a unique restriction site of the vector carrying the marker gene.

To 50 µL of a 60 mg/mL 1 µm gold particle suspension is added (in order): 5 µL DNA (1 µg/µL), 20 µl spermidine (0.1 M), and 50 µL $CaCl_2$ (2.5 M). The particle preparation is then agitated for three minutes, spun in a microfuge for 10 seconds and the supernatant removed. The DNA-coated particles are then washed once in 400 µL 70% ethanol and resuspended in 40 µL of anhydrous ethanol. The DNA/particle suspension can be sonicated three times for one second each. Five µL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 6

Expression of Chimeric Genes in Microbial Cells

The cDNAs encoding the instant polypeptides can be inserted into the T7 E. coli expression vector pBT430. This vector is a derivative of pET-3a (Rosenberg et al. (1987) Gene 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 µg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 µL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 µg/mL ampicillin. Transformants containing the gene encoding the instant polypeptide are then screened for the correct orientation with respect to the T7 promoter by restriction enzyme analysis.

For high level expression, a plasmid clone with the cDNA insert in the correct orientation relative to the T7 promoter can be transformed into E. coli strain BL21 (DE3) (Studier et al. (1986) J. Mol. Biol. 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 µL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One µg of protein from the soluble fraction of the culture can be separated by SDS-polyacrylamide gel electrophoresis. Gels can be observed for protein bands migrating at the expected molecular weight.

Example 7

Assaying Caffeoyl-CoA O-Methyltransferase Activity

The polypeptides described herein may be produced using any number of methods known to those skilled in the art. Such methods include, but are not limited to, expression in bacteria as described in Example 6, or expression in eukaryotic cell culture, in planta, and using viral expression systems in suitably infected organisms or cell lines. The instant polypeptides may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("$(His)_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant polypeptides, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the instant polypeptides are expressed as fusion proteins, the purification protocol may include the use of an affinity resin which is specific for the fusion protein tag attached to the expressed enzyme or an affinity resin containing ligands which are specific for the enzyme. For example, the instant polypeptides may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays to verify over- or underexpression of functional caffeoyl-CoA O-methyltransferase protein in transgenic plants and transformed bacterial cells. Assays may be conducted under well known experimental conditions which permit optimal enzymatic activity. For example, assays for caffeoyl-CoA O-methyltransferase are presented by Martz et al. (1998) *Plant Mol Biol* 36:427–437.

Various modifications of the invention in addition to those shown and described herein will be apparent to those skilled in the art from the foregoing description. Such modifications are also intended to fall within the scope of the appended claims.

The disclosure of each reference set forth above is incorporated herein by reference in its entirety.

What is claimed is:

1. An isolated polynucleotide comprising:
   (a) a first nucleotide sequence encoding a first polypeptide having caffeoyl-CoA O-methyltransferase activity, wherein the amino acid sequence of the first polypeptide and the amino acid sequence of SEQ ID NO:14, SEQ ID NO:20, SEQ ID NO:28, SEQ ID NO:32, or SEQ ID NO:44 have at least 80% identity based on the Clustal alignment method,
   (b) a second nucleotide sequence encoding a second polypeptide having caffeoyl-CoA O-methyltransferase activity, wherein the amino acid sequence of the second polypeptide and the amino acid sequence of SEQ ID NO:24 have at least 85% identity based on the Clustal alignment method,
   (c) a third nucleotide sequence encoding a third polypeptide having caffeoyl-CoA O-methyltransferase activity, wherein the amino acid sequence of the third polypeptide and the amino acid sequence of SEQ ID NO:42 have at least 95% identity based on the Clustal alignment method, or
   (d) the complement of the first, second, or third nucleotide sequence.

2. The polynucleotide of claim 1, wherein the amino acid sequence of the first polypeptide and the amino acid sequence of SEQ ID NO:14, SEQ ID NO:20, SEQ ID NO:28, SEQ ID NO:32, or SEQ ID NO:44 have at least 85% identity based on the Clustal alignment method, and wherein the amino acid sequence of the second polypeptide and the amino acid sequence of SEQ ID NO:24 have at least 90% identity based on the Clustal alignment method.

3. The polynucleotide of claim 1, wherein the amino acid sequence of the first polypeptide and the amino acid sequence of SEQ ID NO:14, SEQ ID NO:20, SEQ ID NO:28, SEQ ID NO:32, or SEQ ID NO:44 have at least 90% identity based on the Clustal alignment method, and wherein the amino acid sequence of the second polypeptide and the amino acid sequence of SEQ ID NO:24 have at least 95% identity based on the Clustal alignment method.

4. The polynucleotide of claim 1, wherein the amino acid sequence of the first polypeptide and the amino acid sequence of SEQ ID NO:14, SEQ ID NO:20, SEQ ID NO:28, SEQ ID NO:32, or SEQ ID NO:44 have at least 95% identity based on the Clustal alignment method.

5. The polynucleotide of claim 1, wherein the amino acid sequence of the first polypeptide comprises the amino acid sequence of SEQ ID NO:14, SEQ ID NO:20, SEQ ID NO:28, SEQ ID NO:32, or SEQ ID NO:44, wherein the amino acid sequence of the second polypeptide comprises the amino acid sequence of SEQ ID NO:24, and wherein the amino acid sequence of the third polypeptide comprises the amino acid sequence of SEQ ID NO:42.

6. The polynucleotide of claim 1, wherein the nucleotide sequence of the first polypeptide comprises the nucleotide sequence of SEQ ID NO:13, SEQ ID NO:19, SEQ ID NO:27, SEQ ID NO:31, or SEQ ID NO:43, wherein the nucleotide sequence of the second polypeptide comprises the nucleotide sequence of SEQ ID NO:23, and wherein the nucleotide sequence of the third polypeptide comprises the nucleotide sequence of SEQ ID NO:41.

7. A chimeric gene comprising the polynucleotide of claim 1 operably linked to a regulatory sequence.

8. A vector comprising the polynucleotide of claim 1.

9. A method for transforming a cell comprising transforming a cell with the polynucleotide of claim 1.

10. A cell comprising the chimeric gene of claim 7.

11. A method for producing a plant comprising transforming a plant cell with the polynucleotide of claim 1 and regenerating a plant from the transformed plant cell.

12. A plant comprising the chimeric gene of claim 7.

13. A seed comprising the chimeric gene of claim 7.

14. A method for isolating a polypeptide encoded by the polynucleotide of claim 1 comprising isolating the polypeptide from a cell transformed with the polynucleotide.

* * * * *

UNITED STATES PATENT AND TRADEMARK OFFICE
CERTIFICATE OF CORRECTION

PATENT NO. : 6,465,229 B2
APPLICATION NO. : 09/452239
DATED : October 15, 2002
INVENTOR(S) : Rebecca E. Cahoon, Gary M. Fader and Rafalski J. Antoni It is certified that error appears in the above-identified patent and that said Letters Patent is hereby corrected as shown below:

Replace the entire Col 98 Claim 6 line 57, of the instant patent and replace with the following --The polynucleotide of claim 1, wherein the first nucleotide sequence comprises the nucleotide sequence of SEQ ID NO:13, SEQ ID NO:19, SEQ ID NO:27, SEQ ID NO:31, or SEQ ID NO:43, wherein the second nucleotide sequence comprises the nucleotide sequence of SEQ ID NO:23, and wherein the third nucleotide sequence comprises the nucleotide sequence of SEQ ID NO:41.--

Signed and Sealed this

Eighteenth Day of July, 2006

JON W. DUDAS
*Director of the United States Patent and Trademark Office*

SEQUENCE LISTING

```
<160> NUMBER OF SEQ ID NOS: 50

<210> SEQ ID NO 1
<211> LENGTH: 891
<212> TYPE: DNA
<213> ORGANISM: Zea mays
<220> FEATURE:
<221> NAME/KEY: unsure
<222> LOCATION: (806)
<220> FEATURE:
<221> NAME/KEY: unsure
<222> LOCATION: (810)

<400> SEQUENCE: 1
cgagtacccg acgcgctact agttctattg ccgcacccca gatctccagg agggactcgt      60
tcgttcagct aactacactg cacgcaatgg ccaccacggc gaccgaggcg gcgccggcgc     120
aggagcagca ggccaacggc aacggcgagc agaagacgcg gcactccgag gtcggccaca     180
agagcctgct caagagcgac gacctctacc agtacatcct ggacacgagc gtgtacccgc     240
gggagccgga gagcatgaag gagctccgcg agatcaccgc caagcaccca tggaacctga     300
tgacgacctc cgccgacgag gggcagttcc tgaacatgct catcaagctc atcggcgcca     360
agaagaccat ggagatcggc gtctacaccg gctactcgct cctcgccacc gcgctcgcac     420
tcccggagga cggcacgatc ttggccatgg acatcaaccg cgagaactac gagctaggcc     480
ttccctgcat caacaaggcc ggcgtgggcc acaagatcga cttccgcgag ggccccgcgc     540
tccccgtcct ggacgacctc gtggcggaca aggagcagca cgggtcgttc gacttcgcct     600
tcgtggacgc cgacaaggac aactacctca gctaccacga gcggctcctg aagctggtga     660
ggcccggcgg cctcatcggc tacgacaaca cgctgtggaa cggctccgtc gtgctccccg     720
acgacgcgcc catgcgcaag tacatccgct tctaccgcga cttcgtcctc gccctcaaca     780
gcgcgctcgc cgccgacgac cgcgtnagan tctgccagct ccccgtcggc gacggcgtca     840
cgctctgccg gccgcgtcaa gtgaaaaaaa gaagaagaag aaaaaaaaca t              891

<210> SEQ ID NO 2
<211> LENGTH: 255
<212> TYPE: PRT
<213> ORGANISM: Zea mays
```

```
<220> FEATURE:
<221> NAME/KEY: UNSURE
<222> LOCATION: (242)

<400> SEQUENCE: 2

Met Ala Thr Thr Ala Thr Glu Ala Ala Pro Ala Gln Glu Gln Gln Ala
 1               5                  10                  15

Asn Gly Asn Gly Glu Gln Lys Thr Arg His Ser Glu Val Gly His Lys
             20                  25                  30

Ser Leu Leu Lys Ser Asp Asp Leu Tyr Gln Tyr Ile Leu Asp Thr Ser
         35                  40                  45

Val Tyr Pro Arg Glu Pro Glu Ser Met Lys Glu Leu Arg Glu Ile Thr
     50                  55                  60

Ala Lys His Pro Trp Asn Leu Met Thr Thr Ser Ala Asp Glu Gly Gln
 65                  70                  75                  80

Phe Leu Asn Met Leu Ile Lys Leu Ile Gly Ala Lys Lys Thr Met Glu
                 85                  90                  95

Ile Gly Val Tyr Thr Gly Tyr Ser Leu Leu Ala Thr Ala Leu Ala Leu
            100                 105                 110

Pro Glu Asp Gly Thr Ile Leu Ala Met Asp Ile Asn Arg Glu Asn Tyr
        115                 120                 125

Glu Leu Gly Leu Pro Cys Ile Asn Lys Ala Gly Val Gly His Lys Ile
    130                 135                 140

Asp Phe Arg Glu Gly Pro Ala Leu Pro Val Leu Asp Asp Leu Val Ala
145                 150                 155                 160

Asp Lys Glu Gln His Gly Ser Phe Asp Phe Ala Phe Val Asp Ala Asp
                165                 170                 175

Lys Asp Asn Tyr Leu Ser Tyr His Glu Arg Leu Leu Lys Leu Val Arg
            180                 185                 190

Pro Gly Gly Leu Ile Gly Tyr Asp Asn Thr Leu Trp Asn Gly Ser Val
        195                 200                 205

Val Leu Pro Asp Asp Ala Pro Met Arg Lys Tyr Ile Arg Phe Tyr Arg
    210                 215                 220

Asp Phe Val Leu Ala Leu Asn Ser Ala Leu Ala Ala Asp Asp Arg Val
225                 230                 235                 240

Arg Xaa Cys Gln Leu Pro Val Gly Asp Gly Val Thr Leu Cys Arg
                245                 250                 255

<210> SEQ ID NO 3
<211> LENGTH: 1146
<212> TYPE: DNA
<213> ORGANISM: Zea mays

<400> SEQUENCE: 3
gcacgagcga gtacccgacg cgctagctag ttctattgcc gcaccccaga tctccaggag    60
ggactcgttc gttcagctaa ctacactgca cgcaatggcc accacggcga ccgaggcggc   120
gccggcgcag gagcagcagg ccaacggcaa cggcgagcag aagacgcggc actccgaggt   180
cggccacaag agcctgctca gagcgacgac cctctaccag tacatcctgg acacgagcgt   240
gtacccgcgg gagccggaga gcatgaagga gctccgcgag atcaccgcca agcacccatg   300
gaacctgatg acgacctccg ccgacgaggg gcagttcctg aacatgctca tcaagctcat   360
cggcgccaag aagaccatgg agatcggcgt ctacaccggc tactcccctcc tcgccacggc   420 gctcgccctc ccggaggacg gcacgatctt ggccatggac atcaaccgcg agaactacga   480
gctgggcctg ccctgcatcg agaaggccgg cgtcgcccac aagatcgact tccgcgaggg   540
```

```
tcccgcgctc cccgtcctcg acgacctcat cgcggaggag aagaaccacg ggtcgttcga    600
cttcgtcttc gtggacgccg acaaggacaa ctacctcaac taccacgagc ggctgctgaa    660
gctggtgaag ctgggcggcc tcatcggcta cgacaacacg ctgtggaacg gctccgtcgt    720
gctccccgac gacgcgccca tgcgcaagta catccgcttc taccgcgact tcgtgctcgt    780
cctcaacaag gcgctcgccg ccgacgaccg cgtcgagatc tgccagctcc ccgtcggcga    840
cggcgtcacc ctctgccgcc gcgtcaagtg aaaacatggc ctggcctggc ctgccccacc    900
accgccaccg acgcgccgc cggccgcatc ctcattccaa tcataataga cgaccccgcag   960 cattaattat ccaccggctt ttttttttggc tctttcttgc ccctgtaatc tttctcctcc   1020
tcttccttct tgggaattgt cgccgccgtt tcgatacgta aatcacgaga tcggtaatac   1080
agtaatgctc ctcaatttta caaaaaaaaa aaaaaaaaaa aaaaaaaaaa aaaaaaaaaa   1140
aaaaaa                                                               1146
```

<210> SEQ ID NO 4
<211> LENGTH: 258
<212> TYPE: PRT
<213> ORGANISM: Zea mays

<400> SEQUENCE: 4

```
Met Ala Thr Thr Ala Thr Glu Ala Ala Pro Ala Gln Glu Gln Gln Ala
 1               5                  10                  15

Asn Gly Asn Gly Glu Gln Lys Thr Arg His Ser Glu Val Gly His Lys
            20                  25                  30

Ser Leu Leu Lys Ser Asp Asp Leu Tyr Gln Tyr Ile Leu Asp Thr Ser
        35                  40                  45

Val Tyr Pro Arg Glu Pro Glu Ser Met Lys Glu Leu Arg Glu Ile Thr
    50                  55                  60

Ala Lys His Pro Trp Asn Leu Met Thr Thr Ser Ala Asp Glu Gly Gln
65                  70                  75                  80

Phe Leu Asn Met Leu Ile Lys Leu Ile Gly Ala Lys Lys Thr Met Glu
                85                  90                  95

Ile Gly Val Tyr Thr Gly Tyr Ser Leu Leu Ala Thr Ala Leu Ala Leu
           100                 105                 110

Pro Glu Asp Gly Thr Ile Leu Ala Met Asp Ile Asn Arg Glu Asn Tyr
       115                 120                 125

Glu Leu Gly Leu Pro Cys Ile Glu Lys Ala Gly Val Ala His Lys Ile
   130                 135                 140

Asp Phe Arg Glu Gly Pro Ala Leu Pro Val Leu Asp Asp Leu Ile Ala
145                 150                 155                 160

Glu Glu Lys Asn His Gly Ser Phe Asp Phe Val Phe Val Asp Ala Asp
                165                 170                 175

Lys Asp Asn Tyr Leu Asn Tyr His Glu Arg Leu Leu Lys Leu Val Lys
            180                 185                 190

Leu Gly Gly Leu Ile Gly Tyr Asp Asn Thr Leu Trp Asn Gly Ser Val
        195                 200                 205

Val Leu Pro Asp Asp Ala Pro Met Arg Lys Tyr Ile Arg Phe Tyr Arg
    210                 215                 220

Asp Phe Val Leu Val Leu Asn Lys Ala Leu Ala Ala Asp Asp Arg Val
225                 230                 235                 240

Glu Ile Cys Gln Leu Pro Val Gly Asp Gly Val Thr Leu Cys Arg Arg
                245                 250                 255
```

Val Lys

<210> SEQ ID NO 5
<211> LENGTH: 1057
<212> TYPE: DNA
<213> ORGANISM: Zea mays

<400> SEQUENCE: 5

| | | | | | |
|---|---|---|---|---|---|
| gcagcgccgc | gagccacagc | tagcaccacc | accttgcacc | gcacccgcac | cgagacgaac | 60 |
| agatcgacca | tggctgccgg | cggcgacgac | accaccatcg | cgcaggtcca | cagcggcatc | 120 |
| gacagcagca | acaagacgct | gctcaagagc | gaggccctct | acaagtacgt | gctggacacg | 180 |
| tcggtgctgc | cgcacgagcc | ggagagcatg | cgtgagctgc | ggctggtgac | cgacaagcac | 240 |
| gagtgggggt | tcatgcagtc | gtccccggac | gaggcgtcgc | tgctgcggat | gctgatcaag | 300 |
| ctgagcggcg | cgcgccgcac | cctggaggtg | ggcgtgttca | cgggctactc | gctgctggcg | 360 |
| acggctctgg | cgctgcccgc | cgacggcaag | gtcatcgcat | tcgacgtgag | ccgcgagtac | 420 |
| tacgacatcg | gccgcccctt | catcgagcgc | gccggggtgg | cgggcaaggt | ggacttccgg | 480 |
| gagggcccgg | cgctggagca | gctggacgag | ctcctcgccg | acccggccaa | ccacggcgcc | 540 |
| ttcgacttcg | ccttcgtcga | cgccgacaag | cctaactacg | tccggtacca | cgagcagctg | 600 |
| ctccgcctgg | tgcgcgtcgg | gggtaccgtc | gtgtacgaca | acacgctgtg | ggccggtact | 660 |
| gtggcgcttc | cccccgacgc | gccgctcagc | gacctcgacc | gcaggttctc | cgccgccatc | 720 |
| agggaactca | acgtccggct | ttctcaggat | ccccgcgtcg | aggtctgcca | gctcgccatc | 780 |
| gccgacggcg | tcaccatctg | ccgccgcgtc | gtctgatgtg | atgatgatcc | gacgaccaag | 840 |
| atcatatatc | attcgctcgt | cgtctctgtc | atctttcaac | tgcctgcccg | ccgctgtccg | 900 |
| ctgccgtcgt | caattaataa | tgcatggttc | ttgttctttt | tttttttttg | tacttgcact | 960 |
| gtgtgtgttg | agttgaacat | ccggcgatgt | actgcaacaa | ctggaatgca | atgcaacatc | 1020 |
| atgcgtgcaa | aaaaaaaaa | aaaaaaaaa | aaaaaaa | | | 1057 |

<210> SEQ ID NO 6
<211> LENGTH: 248
<212> TYPE: PRT
<213> ORGANISM: Zea mays

<400> SEQUENCE: 6

Met Ala Ala Gly Gly Asp Asp Thr Thr Ile Ala Gln Val His Ser Gly
 1               5                  10                  15

Ile Asp Ser Ser Asn Lys Thr Leu Leu Lys Ser Glu Ala Leu Tyr Lys
             20                  25                  30

Tyr Val Leu Asp Thr Ser Val Leu Pro His Glu Pro Glu Ser Met Arg
         35                  40                  45

Glu Leu Arg Leu Val Thr Asp Lys His Glu Trp Gly Phe Met Gln Ser
     50                  55                  60

Ser Pro Asp Glu Ala Ser Leu Leu Arg Met Leu Ile Lys Leu Ser Gly
 65                  70                  75                  80

Ala Arg Arg Thr Leu Glu Val Gly Val Phe Thr Gly Tyr Ser Leu Leu
                 85                  90                  95

Ala Thr Ala Leu Ala Leu Pro Ala Asp Gly Lys Val Ile Ala Phe Asp
            100                 105                 110

Val Ser Arg Glu Tyr Tyr Asp Ile Gly Arg Pro Phe Ile Glu Arg Ala
        115                 120                 125

Gly Val Ala Gly Lys Val Asp Phe Arg Glu Gly Pro Ala Leu Glu Gln

```
                130                 135                 140
Leu Asp Glu Leu Leu Ala Asp Pro Ala Asn His Gly Ala Phe Asp Phe
145                 150                 155                 160

Ala Phe Val Asp Ala Asp Lys Pro Asn Tyr Val Arg Tyr His Glu Gln
                165                 170                 175

Leu Leu Arg Leu Val Arg Val Gly Thr Val Val Tyr Asp Asn Thr
                180                 185                 190

Leu Trp Ala Gly Thr Val Ala Leu Pro Pro Asp Ala Pro Leu Ser Asp
                195                 200                 205

Leu Asp Arg Arg Phe Ser Ala Ala Ile Arg Glu Leu Asn Val Arg Leu
                210                 215                 220

Ser Gln Asp Pro Arg Val Glu Val Cys Gln Leu Ala Ile Ala Asp Gly
225                 230                 235                 240

Val Thr Ile Cys Arg Arg Val Val
                245

<210> SEQ ID NO 7
<211> LENGTH: 923
<212> TYPE: DNA
<213> ORGANISM: Zea mays
<220> FEATURE:
<221> NAME/KEY: unsure
<222> LOCATION: (887)
<220> FEATURE:
<221> NAME/KEY: unsure
<222> LOCATION: (895)
<220> FEATURE:
<221> NAME/KEY: unsure
<222> LOCATION: (914)

<400> SEQUENCE: 7
acggcgatag caaaaccttc cgtcggagga tggcttccgc cggcgctgga gaagggaagg      60
agacggctgc cgggagcagc ctccacagca agactctcct caagagccaa ccactgtacc     120
agtacatact ggaatccacc gtcttcccac gcgagccgga ctgcctgcgg agctccgcg     180
tcgccaccgc cacccacccc atggcgggca tggctgcgtc gccggacgag gtgcagctgc     240
tgcagctcct gatcgagatt cttggcgcca agaacgccat cgaggttggc gtcttcaccg     300
ggtactcgct gctcgccacc gccctcgccc tccccgacga cggcaagatt gtggccatcg     360
acgttacccg cgagagctac gaccagatag gtcgccggt gatcgagaag gccggcgtgg     420
cgcacaagat cgacttccgc gtcgggctcg cgctgcccgt gctggaccag atggtggccg     480
aggagggaa caagggcaag ttcgacttcg cgttcgtgga cgcggacaag gtgaacttcc     540
tcaactacca cgagcggctg ctgcagctgc tcagggtcgg gggcctcatc gcctacgaca     600
acacgctgtg gggcggctcc gtggccgcgt ccccgacga ccgctctcc gagcgggacc     660
gcgcgctcgc tgtgaccacc agggagttca acgcggccg ggccgccgat ccccgcgttc     720
acgtctgcca ggtcgccatc gccgacgggc tcacgctgtg ccgccgcgtc gcctgatccg     780
tatccggtta tccgcctcga aatacagcag agttgggggc tgttcgctga cactgctgtg     840
agctctgtgc ttgaaatggc catggtctgt aataacgaat ggggttnagc gaaantaaat     900
ccaccagcgc gtantgttgt tca                                             923

<210> SEQ ID NO 8
<211> LENGTH: 248
<212> TYPE: PRT
<213> ORGANISM: Zea mays

<400> SEQUENCE: 8
```

-continued

```
Met Ala Ser Ala Gly Ala Gly Glu Gly Lys Glu Thr Ala Ala Gly Ser
 1               5                  10                  15

Ser Leu His Ser Lys Thr Leu Leu Lys Ser Gln Pro Leu Tyr Gln Tyr
            20                  25                  30

Ile Leu Glu Ser Thr Val Phe Pro Arg Glu Pro Asp Cys Leu Arg Glu
         35                  40                  45

Leu Arg Val Ala Thr Ala Thr His Pro Met Ala Gly Met Ala Ala Ser
     50                  55                  60

Pro Asp Glu Val Gln Leu Leu Gln Leu Leu Ile Glu Ile Leu Gly Ala
 65                  70                  75                  80

Lys Asn Ala Ile Glu Val Gly Val Phe Thr Gly Tyr Ser Leu Leu Ala
                 85                  90                  95

Thr Ala Leu Ala Leu Pro Asp Asp Gly Lys Ile Val Ala Ile Asp Val
            100                 105                 110

Thr Arg Glu Ser Tyr Asp Gln Ile Gly Ser Pro Val Ile Glu Lys Ala
        115                 120                 125

Gly Val Ala His Lys Ile Asp Phe Arg Val Gly Leu Ala Leu Pro Val
130                 135                 140

Leu Asp Gln Met Val Ala Glu Glu Gly Asn Lys Gly Lys Phe Asp Phe
145                 150                 155                 160

Ala Phe Val Asp Ala Asp Lys Val Asn Phe Leu Asn Tyr His Glu Arg
                165                 170                 175

Leu Leu Gln Leu Leu Arg Val Gly Gly Leu Ile Ala Tyr Asp Asn Thr
            180                 185                 190

Leu Trp Gly Gly Ser Val Ala Ala Ser Pro Asp Glu Pro Leu Ser Glu
        195                 200                 205

Arg Asp Arg Ala Leu Ala Val Thr Thr Arg Glu Phe Asn Ala Ala Val
    210                 215                 220

Ala Ala Asp Pro Arg Val His Val Cys Gln Val Ala Ile Ala Asp Gly
225                 230                 235                 240

Leu Thr Leu Cys Arg Arg Val Ala
                245
```

<210> SEQ ID NO 9
<211> LENGTH: 510
<212> TYPE: DNA
<213> ORGANISM: Oryza sativa
<220> FEATURE:
<221> NAME/KEY: unsure
<222> LOCATION: (482)
<220> FEATURE:
<221> NAME/KEY: unsure
<222> LOCATION: (507)

<400> SEQUENCE: 9

```
cttacatgta agctcgtgcc gaattcggca cgagcttaca atcgaagcaa gctgctacac        60
agatctcacg acatggccga ggcggcgtcg gcggcggcgg cggcgacgac ggagcaggcg       120
aatgggagca gcgcggcgga gcagaagacg cggcactcgg aggtcggcca caagagcctc       180
ctcaagagcg acgatctcta ccagtacatc ctggagacga gcgtgtaccc gcgcgagcac       240
gagtgcatga aggagctccg cgaggtcacc gccaaccacc catggaacct gatgacgacg       300
tcggcggacg agggcaatt cctgaacctg ctgctgaagc tcatcggcgc caagaagacc       360
atggagatcg gcgtctacac cggtactcc tcctcgcca cgccctcgc catcccgac        420 gacggcacga tcttggcgat ggacatcaac cgggagaact acaactgggg ctcccgtcga       480
```
tngaagaaag gcgggagtgg cgcaaanatt                                      510

<210> SEQ ID NO 10
<211> LENGTH: 133
<212> TYPE: PRT
<213> ORGANISM: Oryza sativa

<400> SEQUENCE: 10

Met Ala Glu Ala Ala Ser Ala Ala Ala Ala Thr Thr Glu Gln Ala
 1               5                  10                  15

Asn Gly Ser Ser Gly Gly Glu Gln Lys Thr Arg His Ser Glu Val Gly
            20                  25                  30

His Lys Ser Leu Leu Lys Ser Asp Asp Leu Tyr Gln Tyr Ile Leu Glu
        35                  40                  45

Thr Ser Val Tyr Pro Arg Glu His Glu Cys Met Lys Glu Leu Arg Glu
    50                  55                  60

Val Thr Ala Asn His Pro Trp Asn Leu Met Thr Thr Ser Ala Asp Glu
 65                 70                  75                  80

Gly Gln Phe Leu Asn Leu Leu Leu Lys Leu Ile Gly Ala Lys Lys Thr
                85                  90                  95

Met Gly Asp Arg Arg Leu His Arg Leu Ser Leu Leu Ala Asn Ala Leu
            100                 105                 110

Ala Ile Pro Asp Asp Gly Thr Ile Leu Ala Met Asp Ile Asn Arg Glu
        115                 120                 125

Asn Tyr Asn Trp Gly
    130

<210> SEQ ID NO 11
<211> LENGTH: 1058
<212> TYPE: DNA
<213> ORGANISM: Oryza sativa

<400> SEQUENCE: 11
gcacgagctt acatgtaagc tcgtgccgaa ttcggcacga gcttacaatc gaagcaagct    60
gctacacaga tctcacgaca tggccgaggc ggcgtcggcg gcggcggcgg cgacgacgga   120
gcaggcgaat gggagcagcg gcggcgagca aaagacgcgg cactcggagg tcggccacaa   180
gagcctcctc aagagcgacg atctctacca gtacatcctg gagacgagcg tgtacccgcg   240
cgagcacgag tgcatgaagg agctccgcga ggtcaccgcc aaccacccat ggaacctgat   300
gacgacgtcg gcggacgagg gcaattcct gaacctgctg ctgaagctca tcggcgccaa   360
gaagaccatg gagatcggcg tctacaccgg ctactccctc ctcgccaccg ccctcgccat   420
ccccgacgac ggcacgatct ggcgatgga catcaaccgg gagaactacg agctggggct   480
cccgtcgatc gagaaggcgg gagtggcgca agatcgac ttccgggagg acccgcgct    540
gccggtgctg gaccagctgg tggaggagga gggcaaccat gggtcgttcg acttcgtgtt   600
cgtcgacgcc gacaaggaca actacctcaa ctaccacgag cggctgatga agctggtcaa   660
ggtcggcggc ctcgtcggct acgacaacac gctctggaac ggctccgtcg tgctccccgc   720
cgacgccccc atgcgcaagt acatccgcta ctaccgcgac ttcgtgctcg agctcaacaa   780
ggccctcgcc gccgaccacc gcgtcagat ctgccagctc cccgtcggcg acggcatcac   840
cctctgccgc cgcgtcaagt gagcccgccg ccgccgcgag tgcgactccg ccgatgccc    900
aagaactagt cattttaaat ttataaatta aactaaatt gtataatttt tgcctttttt    960
ttaatttgca agctactgga aaatgttatt taatatatgt ataaatgtcg agacaataat  1020

```
attattgcat tataaaaaaa aaaaaaaaaa aaaaaaaa                              1058
```

<210> SEQ ID NO 12
<211> LENGTH: 260
<212> TYPE: PRT
<213> ORGANISM: Oryza sativa

<400> SEQUENCE: 12

```
Met Ala Glu Ala Ala Ser Ala Ala Ala Ala Thr Thr Glu Gln Ala
  1               5                  10                  15

Asn Gly Ser Ser Gly Gly Glu Gln Lys Thr Arg His Ser Glu Val Gly
             20                  25                  30

His Lys Ser Leu Leu Lys Ser Asp Asp Leu Tyr Gln Tyr Ile Leu Glu
         35                  40                  45

Thr Ser Val Tyr Pro Arg Glu His Glu Cys Met Lys Glu Leu Arg Glu
     50                  55                  60

Val Thr Ala Asn His Pro Trp Asn Leu Met Thr Thr Ser Ala Asp Glu
 65                  70                  75                  80

Gly Gln Phe Leu Asn Leu Leu Lys Leu Ile Gly Ala Lys Lys Thr
                 85                  90                  95

Met Glu Ile Gly Val Tyr Thr Gly Tyr Ser Leu Leu Ala Thr Ala Leu
                100                 105                 110

Ala Ile Pro Asp Asp Gly Thr Ile Leu Ala Met Asp Ile Asn Arg Glu
            115                 120                 125

Asn Tyr Glu Leu Gly Leu Pro Ser Ile Glu Lys Ala Gly Val Ala His
        130                 135                 140

Lys Ile Asp Phe Arg Glu Gly Pro Ala Leu Pro Val Leu Asp Gln Leu
145                 150                 155                 160

Val Glu Glu Glu Gly Asn His Gly Ser Phe Asp Phe Val Phe Val Asp
                165                 170                 175

Ala Asp Lys Asp Asn Tyr Leu Asn Tyr His Glu Arg Leu Met Lys Leu
            180                 185                 190

Val Lys Val Gly Gly Leu Val Gly Tyr Asp Asn Thr Leu Trp Asn Gly
        195                 200                 205

Ser Val Val Leu Pro Ala Asp Ala Pro Met Arg Lys Tyr Ile Arg Tyr
    210                 215                 220

Tyr Arg Asp Phe Val Leu Glu Leu Asn Lys Ala Leu Ala Asp His
225                 230                 235                 240

Arg Val Glu Ile Cys Gln Leu Pro Val Gly Asp Gly Ile Thr Leu Cys
                245                 250                 255

Arg Arg Val Lys
            260
```

<210> SEQ ID NO 13
<211> LENGTH: 997
<212> TYPE: DNA
<213> ORGANISM: Oryza sativa
<220> FEATURE:
<221> NAME/KEY: unsure
<222> LOCATION: (483)

<400> SEQUENCE: 13

```
ctcgcaccac caccagcagc tcaagcagca acagctcaaa cggaggaaga tctcatcgcc     60
atgacgaccg gcaatggcga cgcaccggtg atcaagaacg cccacagcga catcgacagc    120
accaacaaga cgctgctcaa gagcgacgcc ctgtacaagt atgtcctgga cacgacggtg    180
ctgccacggg agccggagtg catgcgcgat ctgcgcctca tcacggacaa gcaccagtgg    240
```

```
gggttcatgc agtcgtcggc ggatgaggcg cagctgctgg ggatgctgct gaagatggcc      300
ggagcgaaga ggacaatcga ggtgggtgtc ttcaccggct actcgctgct ggcgacggcg      360
ctggcgctgc cggaggacgg gaaggtggtg gcgatcgacc cggacaggga gagctacgag      420
atcgggcggc cgttcttgga gaaagccggg gtggcgcaca aggtggactt cccaagggga      480 aagggctgg agaagctgga cgagctgctc gccgaggagg cggcggcggg gcgcgaggcg       540
gcgttcgact tcgcgttcgt ggacgcggac aagcccaact acgtcaagta ccacgagcag      600
ctgctgcagc tggtgcgcgt cggcgggcac atcgtgtacg acaacacgct gtgggccggc      660
acggtggcgc tgccgccgga cacgccgctg tcggacctgg accggaggtt ctccgtcgcc      720
atcagggacc tcaactccag gctcgccgcc gacccgcgca tcgacgtctg ccaactcgcc      780
atcgccgacg ggatcaccat ctgccgccgc ctcgtgtgag gtcgagaccg agaccttacc      840
ggccgatcca tccatcgctc tcgcgtgatt aattaacgtg tgttgctgta ctcttctact      900
gctacaacta tactattact tccttaattg ccgcttaaat tttcctatac gtgtttcaat      960
caatgagatt attatattct tcgagcaaaa aaaaaaa                              997
```

<210> SEQ ID NO 14
<211> LENGTH: 252
<212> TYPE: PRT
<213> ORGANISM: Oryza sativa
<220> FEATURE:
<221> NAME/KEY: UNSURE
<222> LOCATION: (141)

<400> SEQUENCE: 14

```
Met Thr Thr Gly Asn Gly Asp Ala Pro Val Ile Lys Asn Ala His Ser
 1               5                  10                  15

Asp Ile Asp Ser Thr Asn Lys Thr Leu Leu Lys Ser Asp Ala Leu Tyr
            20                  25                  30

Lys Tyr Val Leu Asp Thr Thr Val Leu Pro Arg Glu Pro Glu Cys Met
        35                  40                  45

Arg Asp Leu Arg Leu Ile Thr Asp Lys His Gln Trp Gly Phe Met Gln
    50                  55                  60

Ser Ser Ala Asp Glu Ala Gln Leu Leu Gly Met Leu Leu Lys Met Ala
65                  70                  75                  80

Gly Ala Lys Arg Thr Ile Glu Val Gly Val Phe Thr Gly Tyr Ser Leu
                85                  90                  95

Leu Ala Thr Ala Leu Ala Leu Pro Glu Asp Gly Lys Val Val Ala Ile
            100                 105                 110

Asp Pro Asp Arg Glu Ser Tyr Glu Ile Gly Arg Pro Phe Leu Glu Lys
        115                 120                 125

Ala Gly Val Ala His Lys Val Asp Phe Pro Arg Gly Xaa Gly Leu Glu
    130                 135                 140

Lys Leu Asp Glu Leu Leu Ala Glu Ala Ala Ala Gly Arg Glu Ala
145                 150                 155                 160

Ala Phe Asp Phe Ala Phe Val Asp Ala Asp Lys Pro Asn Tyr Val Lys
                165                 170                 175

Tyr His Glu Gln Leu Leu Gln Leu Val Arg Val Gly Gly His Ile Val
            180                 185                 190

Tyr Asp Asn Thr Leu Trp Ala Gly Thr Val Ala Leu Pro Pro Asp Thr
        195                 200                 205

Pro Leu Ser Asp Leu Asp Arg Arg Phe Ser Val Ala Ile Arg Asp Leu
    210                 215                 220
```

```
Asn Ser Arg Leu Ala Ala Asp Pro Arg Ile Asp Val Cys Gln Leu Ala
225                 230                 235                 240

Ile Ala Asp Gly Ile Thr Ile Cys Arg Arg Leu Val
                245                 250
```

<210> SEQ ID NO 15
<211> LENGTH: 508
<212> TYPE: DNA
<213> ORGANISM: Oryza sativa
<220> FEATURE:
<221> NAME/KEY: unsure
<222> LOCATION: (434)
<220> FEATURE:
<221> NAME/KEY: unsure
<222> LOCATION: (439)
<220> FEATURE:
<221> NAME/KEY: unsure
<222> LOCATION: (485)
<220> FEATURE:
<221> NAME/KEY: unsure
<222> LOCATION: (491)
<220> FEATURE:
<221> NAME/KEY: unsure
<222> LOCATION: (493)
<220> FEATURE:
<221> NAME/KEY: unsure
<222> LOCATION: (499)
<220> FEATURE:
<221> NAME/KEY: unsure
<222> LOCATION: (501)

<400> SEQUENCE: 15

```
cttacagcac actctaggcg gctgaagcga acgacaccgg cgtcaagagt atcaagcacg    60
gccatggcgg cggcgaacgg cgatgccagc catggcgcca acggcggcat tcagattcag   120
tccaaggaga tgaagacggc catccacagc aacgatagcc ccaagaccct cctcaagagt   180
gaatccctcc acgagtacat gctgaacacg atggtgtacc cgcgggagaa cgagttcatg   240
cgcgagctcc gcctcatcac cagcgagcac acctatgggt tcatgtcgtc gccgccggag   300
gaagggcagc tgctgtcgct gctgctgaac ctgacaggcg ccaagaacac catcgaggtg   360
ggcgtgttca ccggctgctc cgtgctcgcc acggcgctcg catcccggac gacggcaagt   420
ccgtccatcg actnaaccng gattattcga cttcggctcc cctcatcaag aggcggggtc   480
cccanaggtc nanttcgcna ngggccca                                      508
```

<210> SEQ ID NO 16
<211> LENGTH: 113
<212> TYPE: PRT
<213> ORGANISM: Oryza sativa

<400> SEQUENCE: 16

```
Met Ala Ala Ala Asn Gly Asp Ala Ser His Gly Ala Asn Gly Gly Ile
1               5                   10                  15

Gln Ile Gln Ser Lys Glu Met Lys Thr Ala Ile His Ser Asn Asp Ser
            20                  25                  30

Pro Lys Thr Leu Leu Lys Ser Glu Ser Leu His Glu Tyr Met Leu Asn
        35                  40                  45

Thr Met Val Tyr Pro Arg Glu Asn Glu Phe Met Arg Glu Leu Arg Leu
    50                  55                  60

Ile Thr Ser Glu His Thr Tyr Gly Phe Met Ser Ser Pro Pro Glu Glu
65                  70                  75                  80

Gly Gln Leu Leu Ser Leu Leu Leu Asn Leu Thr Gly Ala Lys Asn Thr
                85                  90                  95
```

```
Ile Glu Val Gly Val Phe Thr Gly Cys Ser Val Leu Ala Thr Ala Leu
            100                 105                 110

Ala

<210> SEQ ID NO 17
<211> LENGTH: 931
<212> TYPE: DNA
<213> ORGANISM: Glycine max
<220> FEATURE:
<221> NAME/KEY: unsure
<222> LOCATION: (18)

<400> SEQUENCE: 17
caactcttca aagggganaa gaaaaggaaa gaaaactctc aaaaaactat tatagcaatg      60
gcagaacaaa accaaaacca aacaactgaa gctggaaggc accaagaggt tggtcacaag     120
agccttctcc agagtgatgc tctttaccag tatattctgg agacaagtgt ctacccaaga     180
gaacctgaat ccatgaaaga actgagagag ttgacagcaa acacccatg gaacatcatg      240 acaacctctg cagacgaagg gcagttcttg aacatgctcc ttaagctcat caatgccaag     300
aacaccatgg aaattggtgt ctacactggg tattcacttc ttgccaccgc tctcgctctt     360
cctgaagatg gaaagatctt ggccatggac attaacaggg agaattatga attgggtttg     420
cctgtaatta aaaagctgg tgttgaccac aaaattgaat tcagagaagg tcctgctcta     480
ccagttcttg atgaaatgat taagatgag aagaaccatg gaagctatga cttcatcttt      540
gttgatgcgg acaaggacaa ctacctcaac taccacaaga ggttgataga gcttgtaaaa     600
gttgggggcg tgatcgggta cgacaacacc ctatggaacg gatctgtggt ggcaccccct     660
gatgctcctc ttaggaagta tgttaggtac tacagggact tcgtgctgga gctcaacaaa     720
gccctcgctg tggaccccag gatcgagatt tgcatgctcc cggttggtga tggaatcact     780
atctgccgtc ggatcaagtg atttctgatc atcataatcg tggaccaccg ttgcttcttc     840
tgcacaccct atagtgatga ctggtcatca ttgagtggca cctgctaatg catttaaaag     900
caatcaatac ttttctttca aaaaaaaaa a                                     931

<210> SEQ ID NO 18
<211> LENGTH: 247
<212> TYPE: PRT
<213> ORGANISM: Glycine max

<400> SEQUENCE: 18

Met Ala Glu Gln Asn Gln Asn Gln Thr Thr Glu Ala Gly Arg His Gln
  1               5                  10                  15

Glu Val Gly His Lys Ser Leu Leu Gln Ser Asp Ala Leu Tyr Gln Tyr
                 20                  25                  30

Ile Leu Glu Thr Ser Val Tyr Pro Arg Glu Pro Glu Ser Met Lys Glu
             35                  40                  45

Leu Arg Glu Leu Thr Ala Lys His Pro Trp Asn Ile Met Thr Thr Ser
         50                  55                  60

Ala Asp Glu Gly Gln Phe Leu Asn Met Leu Leu Lys Leu Ile Asn Ala
 65                  70                  75                  80

Lys Asn Thr Met Glu Ile Gly Val Tyr Thr Gly Tyr Ser Leu Leu Ala
                 85                  90                  95

Thr Ala Leu Ala Leu Pro Glu Asp Gly Lys Ile Leu Ala Met Asp Ile
            100                 105                 110

Asn Arg Glu Asn Tyr Glu Leu Gly Leu Pro Val Ile Lys Lys Ala Gly
```

-continued

```
                  115                 120                     125
    Val Asp His Lys Ile Glu Phe Arg Glu Gly Pro Ala Leu Pro Val Leu
        130                 135                 140

Asp Glu Met Ile Lys Asp Glu Lys Asn His Gly Ser Tyr Asp Phe Ile
    145                 150                 155                 160

Phe Val Asp Ala Asp Lys Asp Asn Tyr Leu Asn Tyr His Lys Arg Leu
                    165                 170                 175

Ile Glu Leu Val Lys Val Gly Val Ile Gly Tyr Asp Asn Thr Leu
                180                 185                 190

Trp Asn Gly Ser Val Val Ala Pro Pro Asp Ala Pro Leu Arg Lys Tyr
                    195                 200                 205

Val Arg Tyr Tyr Arg Asp Phe Val Leu Glu Leu Asn Lys Ala Leu Ala
        210                 215                 220

Val Asp Pro Arg Ile Glu Ile Cys Met Leu Pro Val Gly Asp Gly Ile
    225                 230                 235                 240

Thr Ile Cys Arg Arg Ile Lys
                    245
```

<210> SEQ ID NO 19
<211> LENGTH: 929
<212> TYPE: DNA
<213> ORGANISM: Glycine max
<220> FEATURE:
<221> NAME/KEY: unsure
<222> LOCATION: (851)
<220> FEATURE:
<221> NAME/KEY: unsure
<222> LOCATION: (901)

<400> SEQUENCE: 19

```
gagctaacaa gagattcaag accggcatgg ctaatgaaga ggaacagaaa aaccacctct      60
tcggcatcaa agatctcggt cacaagactc tccttcagag tgatgcactc tatcagtata     120
tacttgaaac cagtgtctat ccaagagagc acgagtgctt gaaagagata cgcaagatga     180
ctgcaaaaca cccactgaac atcatggcaa caccagcaga cgaaggacaa cttctgagca     240
tgcttgttaa gctcacgaat tcaaagaacg ccttggaaat tggtgtattc actggttact     300
ctctgctctc cactgccctg gctcttcccc ctgatgaaa gatcttggct ttggatgtga     360
atcgcgaata ctatgagtta ggattgccaa taattcaaaa agctggagtg gctcacaaga     420
ttgatttcag agaaaggact gctcttccgt tcctgacga gatgcttaaa gatgaaaata     480
aaaagggtcc ttgggtttcg gtttccgtgg atgctgataa ggacaattac ttgaactacc     540
acaagagggt actagagctt gtgaagattg gaggactgat cggatacgat aacaccctat     600
gggctggatc tgtggctgca ccacccgatg caccattgat ggattacatt aagcctcttc     660
gcggccatgt gatggagctc aacaagtatc tggctcaaga ttcgaggatc gagatttgcc     720
agctccccgt gggtgatggg attaccctgt gccgccgcat catctgatca tttctcttca     780
tctagatttt tcatgacaga tattccttca taaaacaggt tgcgtgaata gtggattctc     840
aaatgttcta ntgtcttttc tagatctttg tgtgtatctt gtcacggcta ggaatttagc     900
ngaaaggata caaatcaaca tttatctca                                       929
```

<210> SEQ ID NO 20
<211> LENGTH: 246
<212> TYPE: PRT
<213> ORGANISM: Glycine max

<400> SEQUENCE: 20

```
Met Ala Asn Glu Glu Gln Lys Asn His Leu Phe Gly Ile Lys Asp
 1               5                  10                  15

Leu Gly His Lys Thr Leu Leu Gln Ser Asp Ala Leu Tyr Gln Tyr Ile
                20                  25                  30

Leu Glu Thr Ser Val Tyr Pro Arg Glu His Glu Cys Leu Lys Glu Ile
            35                  40                  45

Arg Lys Met Thr Ala Lys His Pro Leu Asn Ile Met Ala Thr Pro Ala
        50                  55                  60

Asp Glu Gly Gln Leu Leu Ser Met Leu Val Lys Leu Thr Asn Ser Lys
65                  70                  75                  80

Asn Ala Leu Glu Ile Gly Val Phe Thr Gly Tyr Ser Leu Leu Ser Thr
                85                  90                  95

Ala Leu Ala Leu Pro Pro Asp Gly Lys Ile Leu Ala Leu Asp Val Asn
                100                 105                 110

Arg Glu Tyr Tyr Glu Leu Gly Leu Pro Ile Ile Gln Lys Ala Gly Val
            115                 120                 125

Ala His Lys Ile Asp Phe Arg Glu Arg Thr Ala Leu Pro Phe Pro Asp
        130                 135                 140

Glu Met Leu Lys Asp Glu Asn Lys Lys Gly Pro Trp Val Ser Val Ser
145                 150                 155                 160

Val Asp Ala Asp Lys Asp Asn Tyr Leu Asn Tyr His Lys Arg Val Leu
                165                 170                 175

Glu Leu Val Lys Ile Gly Gly Leu Ile Gly Tyr Asp Asn Thr Leu Trp
                180                 185                 190

Ala Gly Ser Val Ala Ala Pro Pro Asp Ala Pro Leu Met Asp Tyr Ile
            195                 200                 205

Lys Pro Leu Arg Gly His Val Met Glu Leu Asn Lys Tyr Leu Ala Gln
        210                 215                 220

Asp Ser Arg Ile Glu Ile Cys Gln Leu Pro Val Gly Asp Gly Ile Thr
225                 230                 235                 240

Leu Cys Arg Arg Ile Ile
                245

<210> SEQ ID NO 21
<211> LENGTH: 980
<212> TYPE: DNA
<213> ORGANISM: Glycine max

<400> SEQUENCE: 21
gcacgaggag ctaacaagag attcaagacc ggcatggcta atgaagagga acagaaaaac    60
cacctcttcg gcatcaaaga tctcggtcac aagactctcc ttcagagtga tgcactctat   120
cagtatatac ttgaaaccag tgtctatcca agagagcacg agtgcttgaa agagatacgc   180
aagatgactg caaaacaccc actgaacatc atggcaacac cagcagacga aggacaactt   240
ctgagcatgc ttgttaagct cacgaattca aagaacgcct ggaaattggt gtattcact    300
ggttactctc tgctctccac tgccctggct cttcccctg atggaaagat cttggctttg   360
gatgtgaatc gcgaatacta tgagttagga ttgccaataa ttcaaaaagc tggagtggct   420
cacaagattg atttcagaga aggacctgct cttccgtttc ttgacgagat gcttaaagat   480
gaaaataaaa agggtcgttg gatttcgtt ttcgtggatg ctgataagga caattacttg   540
aactaccaca gagggtact agagcttgtg aagattggag gactgatcgg atacgataac   600
accctatggg ctggatctgt ggctgcacca cccgatgcac cattgatgga ttacattaag   660
```

-continued

```
cctcttcgcg gccatgtgat ggagctcaac aagtatctgg ctcaagattc gaggatcgag      720
atttgccagc tccccgtggg tgatgggatt accctgtgcc gccgcatcat ctgatcattt      780
tctcttcatc tagattttc atgacagata ttcctttcat taaaacaggt tgcgtgaatg       840
gtggagttct caaatgttct actgtctttt ctagatcttt gtgtgtttct tgtcacgcta      900
gaaatttagc tgaaaggata caaatcaaca tttatcttat ttaaaaaaaa aaaaaaaaa       960 aaaaaaaaaa aaaaaaaaa                                                  980
```

```
<210> SEQ ID NO 22
<211> LENGTH: 246
<212> TYPE: PRT
<213> ORGANISM: Glycine max

<400> SEQUENCE: 22

Met Ala Asn Glu Glu Glu Gln Lys Asn His Leu Phe Gly Ile Lys Asp
  1               5                  10                  15

Leu Gly His Lys Thr Leu Leu Gln Ser Asp Ala Leu Tyr Gln Tyr Ile
             20                  25                  30

Leu Glu Thr Ser Val Tyr Pro Arg Glu His Glu Cys Leu Lys Glu Ile
         35                  40                  45

Arg Lys Met Thr Ala Lys His Pro Leu Asn Ile Met Ala Thr Pro Ala
     50                  55                  60

Asp Glu Gly Gln Leu Leu Ser Met Leu Val Lys Leu Thr Asn Ser Lys
 65                  70                  75                  80

Asn Ala Leu Glu Ile Gly Val Phe Thr Gly Tyr Ser Leu Leu Ser Thr
                 85                  90                  95

Ala Leu Ala Leu Pro Pro Asp Gly Lys Ile Leu Ala Leu Asp Val Asn
            100                 105                 110

Arg Glu Tyr Tyr Glu Leu Gly Leu Pro Ile Ile Gln Lys Ala Gly Val
        115                 120                 125

Ala His Lys Ile Asp Phe Arg Glu Gly Pro Ala Leu Pro Phe Leu Asp
    130                 135                 140

Glu Met Leu Lys Asp Glu Asn Lys Lys Gly Ser Leu Asp Phe Val Phe
145                 150                 155                 160

Val Asp Ala Asp Lys Asp Asn Tyr Leu Asn Tyr His Lys Arg Val Leu
                165                 170                 175

Glu Leu Val Lys Ile Gly Gly Leu Ile Gly Tyr Asp Asn Thr Leu Trp
            180                 185                 190

Ala Gly Ser Val Ala Ala Pro Pro Asp Ala Pro Leu Met Asp Tyr Ile
        195                 200                 205

Lys Pro Leu Arg Gly His Val Met Glu Leu Asn Lys Tyr Leu Ala Gln
    210                 215                 220

Asp Ser Arg Ile Glu Ile Cys Gln Leu Pro Val Gly Asp Gly Ile Thr
225                 230                 235                 240

Leu Cys Arg Arg Ile Ile
                245
```

```
<210> SEQ ID NO 23
<211> LENGTH: 962
<212> TYPE: DNA
<213> ORGANISM: Glycine max
<220> FEATURE:
<221> NAME/KEY: unsure
<222> LOCATION: (22)
<220> FEATURE:
<221> NAME/KEY: unsure
<222> LOCATION: (68)
```

```
<220> FEATURE:
<221> NAME/KEY: unsure
<222> LOCATION: (866)
<220> FEATURE:
<221> NAME/KEY: unsure
<222> LOCATION: (902)
<220> FEATURE:
<221> NAME/KEY: unsure
<222> LOCATION: (905)

<400> SEQUENCE: 23
gagaattcca actgataaaa anaatattca gagaattcca aagacagaga tgactgtcat      60
taaggaanag caacaaccaa accaaatagc tggccacaaa gaacttggtc acaaaagtct     120
ccttcagagc gatgcactct atcagtatat acttgaaacc agtgtgtacc aagagagca     180
tgagagcttg aaggagctac gagagttgac ggaaaaacac ccttggaacc tgatggctac     240
accacctgac gaaggacaac ttctaggcat gctccttaag cttatcaatg ccaagaacac     300
catggaaata ggcgtcttca ctggttactc cttgctttcc actgcccttg ccctcccttc     360
tgacggaaag atcttagcta tggatgttaa ccgggaatat tatgaattgg ggttgcccgt     420
gattgaaaag gctggagtgg ctcacaagat tgacttcaga gaaggacccg ctcttcctct     480
tcttgacgtt ctcattaaag acgaaaagaa taagggagct ttcgatttca tctatgtgga     540
tgctgataag gacaattact tgaactacca caagagggtg attgagcttg tgaagcttgg     600
gggattgatc ggctacgata cacccctatg gaatgggtcc gtggtggccc cacccgatgc     660
tcctctcatg gattatgtta agtattatcg cgattttgtt atggagctca acaaagctct     720
tgcacttgat tcaagggtcg agatttgcca gcttcccgtt ggtgatggga ttaccctgtg     780
ccgccgcatc atctgatcat tccgctcctt ccctcccctt tttacctact tcacctgcca     840
catatgggaa aaacacacct tctacnattt acctaaccct taaaataaac ataagtgtgt     900
cngcntggat attaccccgtt gttgatttta atctctacca ataaatcaaa atgttcctcc     960
tt                                                                    962

<210> SEQ ID NO 24
<211> LENGTH: 248
<212> TYPE: PRT
<213> ORGANISM: Glycine max
<220> FEATURE:
<221> NAME/KEY: UNSURE
<222> LOCATION: (7)

<400> SEQUENCE: 24

Met Thr Val Ile Lys Glu Xaa Gln Gln Pro Asn Gln Ile Ala Gly His
  1               5                  10                  15

Lys Glu Leu Gly His Lys Ser Leu Leu Gln Ser Asp Ala Leu Tyr Gln
                 20                  25                  30

Tyr Ile Leu Glu Thr Ser Val Tyr Pro Arg Glu His Glu Ser Leu Lys
             35                  40                  45

Glu Leu Arg Glu Leu Thr Glu Lys His Pro Trp Asn Leu Met Ala Thr
         50                  55                  60

Pro Pro Asp Glu Gly Gln Leu Leu Gly Met Leu Leu Lys Leu Ile Asn
 65                  70                  75                  80

Ala Lys Asn Thr Met Glu Ile Gly Val Phe Thr Gly Tyr Ser Leu Leu
                 85                  90                  95

Ser Thr Ala Leu Ala Leu Pro Ser Asp Gly Lys Ile Leu Ala Met Asp
                100                 105                 110

Val Asn Arg Glu Tyr Tyr Glu Leu Gly Leu Pro Val Ile Glu Lys Ala
```

```
                115                 120                     125
Gly Val Ala His Lys Ile Asp Phe Arg Glu Gly Pro Ala Leu Pro Leu
        130                 135                 140

Leu Asp Val Leu Ile Lys Asp Glu Lys Asn Lys Gly Ala Phe Asp Phe
145                 150                 155                 160

Ile Tyr Val Asp Ala Asp Lys Asp Asn Tyr Leu Asn Tyr His Lys Arg
                165                 170                 175

Val Ile Glu Leu Val Lys Leu Gly Gly Leu Ile Gly Tyr Asp Asn Thr
            180                 185                 190

Leu Trp Asn Gly Ser Val Val Ala Pro Pro Asp Ala Pro Leu Met Asp
        195                 200                 205

Tyr Val Lys Tyr Tyr Arg Asp Phe Val Met Glu Leu Asn Lys Ala Leu
    210                 215                 220

Ala Leu Asp Ser Arg Val Glu Ile Cys Gln Leu Pro Val Gly Asp Gly
225                 230                 235                 240

Ile Thr Leu Cys Arg Arg Ile Ile
                245
```

<210> SEQ ID NO 25
<211> LENGTH: 1023
<212> TYPE: DNA
<213> ORGANISM: Glycine max

<400> SEQUENCE: 25

```
gcacgaggag aattccaact gataaaaaga atattcagag aattccaaag acagagatga      60
ctgtcattaa ggaagagcaa caaccaaacc aaatagctgg ccacaaagaa cttggtcaca     120
aaagtctcct tcagagcgat gcactctatc agtatatact tgaaaccagt gtgtacccaa     180
gagagcatga gagcttgaag gagctacgag agttgacgga aaaacaccct tggaacctga     240
tggctacacc acctgacgaa ggacaacttc taggcatgcc ccttaagctt atcaatgcca     300
agaacaccat ggaaataggc gtcttcactg gttactcctt gctttccact gcccttgccc     360
tcccttctga cggaaagatc ttagctatgg atgttaaccg ggaatattat gaattggggt     420
tgcccgtgat tgaaaaggct ggagtggctc acaagattga cttcagagaa ggacccgctc     480
ttcctcttct tgacgttctc attaaagacg aaaagaataa gggagctttc gatttcatct     540
atgtggatgc tgataaggac aattacttga actaccacaa gagggtgatt gagcttgtga     600
agcttggggg attgatcggc tacgataaca ccctatggaa tggtccgtg gtggccccac      660
ccgatgctcc tctcatggat tatgttaagt attatcgcga ttttgttatg gagctcaaca     720
aagctcttgc acttgattca agggtcgaga tttgccagct tcccgttggt gatgggatta     780
ccctgtgccg ccgcatcatc tgatcattct gctccttccc tccccttta cctacttcac      840
ctgccacata tggaaaaaac acaaccttct actattttac ctaatcctta aataaacata     900
atgtgtgtct gcttggatag ttactctgtt gttgagtttt agtcttctac gcaattatat     960
tcataatgtt tctcttcctt aaacaaaca catgttttga atcaaaaaaa aaaaaaaaa      1020
aaa                                                                 1023
```

<210> SEQ ID NO 26
<211> LENGTH: 248
<212> TYPE: PRT
<213> ORGANISM: Glycine max

<400> SEQUENCE: 26

Met Thr Val Ile Lys Glu Glu Gln Gln Pro Asn Gln Ile Ala Gly His

```
              1               5              10              15

Lys Glu Leu Gly His Lys Ser Leu Leu Gln Ser Asp Ala Leu Tyr Gln
                         20                  25                  30

Tyr Ile Leu Glu Thr Ser Val Tyr Pro Arg Glu His Glu Ser Leu Lys
                     35                  40                  45

Glu Leu Arg Glu Leu Thr Glu Lys His Pro Trp Asn Leu Met Ala Thr
                 50                  55                  60

Pro Pro Asp Glu Gly Gln Leu Leu Gly Met Leu Leu Lys Leu Ile Asn
         65                  70                  75                  80

Ala Lys Asn Thr Met Glu Ile Gly Val Phe Thr Gly Tyr Ser Leu Leu
                             85                  90                  95

Ser Thr Ala Leu Ala Leu Pro Ser Asp Gly Lys Ile Leu Ala Met Asp
                        100                 105                 110

Val Asn Arg Glu Tyr Tyr Glu Leu Gly Leu Pro Val Ile Glu Lys Ala
                    115                 120                 125

Gly Val Ala His Lys Ile Asp Phe Arg Glu Gly Pro Ala Leu Pro Leu
                130                 135                 140

Leu Asp Val Leu Ile Lys Asp Glu Lys Asn Lys Gly Ala Phe Asp Phe
        145                 150                 155                 160

Ile Tyr Val Asp Ala Asp Lys Asp Asn Tyr Leu Asn Tyr His Lys Arg
                            165                 170                 175

Val Ile Glu Leu Val Lys Leu Gly Gly Leu Ile Gly Tyr Asp Asn Thr
                        180                 185                 190

Leu Trp Asn Gly Ser Val Val Ala Pro Pro Asp Ala Pro Leu Met Asp
                    195                 200                 205

Tyr Val Lys Tyr Arg Asp Phe Val Met Glu Leu Asn Lys Ala Leu
                210                 215                 220

Ala Leu Asp Ser Arg Val Glu Ile Cys Gln Leu Pro Val Gly Asp Gly
        225                 230                 235                 240

Ile Thr Leu Cys Arg Arg Ile Ile
                        245

<210> SEQ ID NO 27
<211> LENGTH: 912
<212> TYPE: DNA
<213> ORGANISM: Glycine max

<400> SEQUENCE: 27
ttcaatcaca tacttcttct cctagatcta gaacttgttg tgaactgaac aacatatata    60
ttctaagctc tttgaactta tccttcactg atcagattca gagaaatgga aaacatcaaa   120
gatccatcaa tttaccgcaa tccagtcata ttgcagagcg aggacttaac caagtatatt   180
ctggaaactg ctgtttaccc tagagaacct gcgcctctaa agagctgag  ggaagccact   240 aataatcacc ttggggcttc attgctact ttacctgaag cgggtcagct aatgacctta   300
cttttgaagc tgttgaatcc caaaaagacc attgaagtgg gagtgtttac tggttattcc   360
cttctcctca ccgcactcaa cattcctcat gatggaaaga ttacagccat agatattaac   420
aggaaaactt atgaggttgg tttaccagtc atcaaaaagg ctggagttga gcacaagatt   480
gatttcatag agtctccagc tctaccaatt ttggatgagc tacttgaaga tcctgcaaat   540
gaaggatctt tgactttgc  cttcattgat gctgacaagg agaactatgt gaactaccat   600
gagaggctta taaagctggt caagattggg gggttgcttg tgtatgacaa cacactgtgg   660
ggtggacgtg tttgctggcc tgaagacaaa gttccaccac acgctagatc agggagggac   720
```

```
gctgcaattg aatttaacaa aacaatcaca aacgattctc gtgttgaatt tgctcttact    780
tccgtagggg atgggctcaa tatttgtagg cgcgttgctt gacttttgtg ttaatgctct    840
gctatcgtat aatttgtatt tctagtagcc acctgaataa acattgcatt ttgtgttcct    900
aaaaaaaaaa aa                                                        912
```

<210> SEQ ID NO 28
<211> LENGTH: 238
<212> TYPE: PRT
<213> ORGANISM: Glycine max

<400> SEQUENCE: 28

```
Met Glu Asn Ile Lys Asp Pro Ser Ile Tyr Arg Asn Pro Val Ile Leu
 1               5                  10                  15

Gln Ser Glu Asp Leu Thr Lys Tyr Ile Leu Glu Thr Ala Val Tyr Pro
            20                  25                  30

Arg Glu Pro Ala Pro Leu Lys Glu Leu Arg Glu Ala Thr Asn Asn His
        35                  40                  45

Pro Trp Gly Phe Ile Ala Thr Leu Pro Glu Ala Gly Gln Leu Met Thr
    50                  55                  60

Leu Leu Leu Lys Leu Leu Asn Pro Lys Lys Thr Ile Glu Val Gly Val
65                  70                  75                  80

Phe Thr Gly Tyr Ser Leu Leu Thr Ala Leu Asn Ile Pro His Asp
                85                  90                  95

Gly Lys Ile Thr Ala Ile Asp Ile Asn Arg Lys Thr Tyr Glu Val Gly
            100                 105                 110

Leu Pro Val Ile Lys Lys Ala Gly Val Glu His Lys Ile Asp Phe Ile
        115                 120                 125

Glu Ser Pro Ala Leu Pro Ile Leu Asp Glu Leu Leu Glu Asp Pro Ala
    130                 135                 140

Asn Glu Gly Ser Phe Asp Phe Ala Phe Ile Asp Ala Asp Lys Glu Asn
145                 150                 155                 160

Tyr Val Asn Tyr His Glu Arg Leu Ile Lys Leu Val Lys Ile Gly Gly
                165                 170                 175

Leu Leu Val Tyr Asp Asn Thr Leu Trp Gly Gly Arg Val Cys Trp Pro
            180                 185                 190

Glu Asp Lys Val Pro Pro His Ala Arg Ser Gly Arg Asp Ala Ala Ile
        195                 200                 205

Glu Phe Asn Lys Thr Ile Thr Asp Ser Arg Val Glu Phe Ala Leu
    210                 215                 220

Thr Ser Val Gly Asp Gly Leu Asn Ile Cys Arg Arg Val Ala
225                 230                 235
```

<210> SEQ ID NO 29
<211> LENGTH: 505
<212> TYPE: DNA
<213> ORGANISM: Glycine max

<400> SEQUENCE: 29

```
agaaggctta acaaagcaca gaatgtcctc taatccagta atactgcaga gtgtgaactt     60
gaccaagtat atactggaga ccagcgttta tccacgagaa gaagagactc tcaaagagct    120
aaggaaagcc actgcaggcc acccttgggg ctttatgggc gctgctcccg atgcgggtca    180
gctaatgacc ttgctcttga agttgttgaa tgctaagaag acaattgaag tgggagtttt    240
tactgggtac tctcttctcc tcactgcact taccattcca gatgatggaa agattatagc    300
```

```
cctgqatcca qacaqaqaaa cttatqaqat aqqattaccq ttcattaaaa aqqctqqtqt      360 aqaqcacaaa qatcqcttca taaqaqtctc cactctaccq ttcttqataa actcqtaqaa      420 qtcttcaaat aaqqaaqttt qctttqcttt qttqtqcqta aaqtactatt qqattacacq      480 aqaqctctta actqtaaqat tqtqq                                            505
```

<210> SEQ ID NO 30
<211> LENGTH: 131
<212> TYPE: PRT
<213> ORGANISM: Glycine max

<400> SEQUENCE: 30

```
Lys His Arg Met Ser Ser Asn Pro Val Ile Leu Gln Ser Val Asn Leu
  1               5                  10                  15

Thr Lys Tyr Ile Leu Glu Thr Ser Val Tyr Pro Arg Glu Glu Glu Thr
             20                  25                  30

Leu Lys Glu Leu Arg Lys Ala Thr Ala Gly His Pro Trp Gly Phe Met
         35                  40                  45

Gly Ala Ala Pro Asp Ala Gly Gln Leu Met Thr Leu Leu Leu Lys Leu
     50                  55                  60

Leu Asn Ala Lys Lys Thr Ile Glu Val Gly Val Phe Thr Gly Tyr Ser
 65                  70                  75                  80

Leu Leu Leu Thr Ala Leu Thr Ile Pro Asp Asp Gly Lys Ile Ile Ala
                 85                  90                  95

Leu Asp Pro Asp Arg Glu Thr Tyr Glu Ile Gly Leu Pro Phe Ile Lys
                100                 105                 110

Lys Ala Gly Val Glu His Lys Asp Arg Phe Ile Arg Val Ser Thr Leu
            115                 120                 125

Pro Phe Leu
    130
```

<210> SEQ ID NO 31
<211> LENGTH: 982
<212> TYPE: DNA
<213> ORGANISM: Glycine max

<400> SEQUENCE: 31

```
gcacgagaga aggcttaaca agcacagaa tgtcctctaa tccagtaata ctgcagagtg       60
tgaacttgac caagtatata ctggagacca gcgtttatcc acgagaagaa gagactctca     120
aagagctaag gaaagccact gcaggccacc cttggggctt tatgggcgct gctcccgatg     180
cgggtcagct aatgaccttg ctcttgaagt tgttgaatgc taagaagaca attgaagtgg     240
gagtttttac tgggtactct cttctcctca ctgcacttac cattccagat gatggaaaga     300
ttatagccct ggatccagac agagaaactt atgagatagg attaccgttc attaaaaagg     360
ctggtgtaga gcacaagatc gacttcatag agtctccagc tctaccqgtt cttgataaac     420 tcgtagaaga tccttcaaat aaggaaagtt ttgactttgc ctttgttgat gccgataaag     480
ataactattg gaattaccac gagaggcttc ttaaactggt aaagattggt gggttaatca     540
tctatgataa cactctctgg ggtggaactg ttgcctggcc tgaagaggat gttcctgtac     600 caaaaggaa attcaggcag ctacactggc ttcaacaa agcaattgct gatgattctc       660
gtgttgaaat ttctgttgtt caataggtg atggcttcac tatctgcagg cgtgctcatt      720
gaacatcatc tgccaatgtt gtattaagat tcaagttaat ttcatgtact atgttttcgt     780
gttttatttt tctctctttt gggagtgggg ggtttactaa atttacgtga taacttgtgg     840
```

```
tataatttga tttacctccg actctggggc ctatgcccta tggtgtgact ctaatgtgaa    900
actgggcgtg tcgctattta tttactagta ctaaataaaa taaaatgttg tgtctatatt    960
ccaaaaaaaa aaaaaaaaaa aa                                             982
```

<210> SEQ ID NO 32
<211> LENGTH: 230
<212> TYPE: PRT
<213> ORGANISM: Glycine max

<400> SEQUENCE: 32

```
Met Ser Ser Asn Pro Val Ile Leu Gln Ser Val Asn Leu Thr Lys Tyr
 1               5                  10                  15

Ile Leu Glu Thr Ser Val Tyr Pro Arg Glu Glu Glu Thr Leu Lys Glu
            20                  25                  30

Leu Arg Lys Ala Thr Ala Gly His Pro Trp Gly Phe Met Gly Ala Ala
        35                  40                  45

Pro Asp Ala Gly Gln Leu Met Thr Leu Leu Lys Leu Leu Asn Ala
    50                  55                  60

Lys Lys Thr Ile Glu Val Gly Val Phe Thr Gly Tyr Ser Leu Leu Leu
 65                  70                  75                  80

Thr Ala Leu Thr Ile Pro Asp Asp Gly Lys Ile Ile Ala Leu Asp Pro
                85                  90                  95

Asp Arg Glu Thr Tyr Glu Ile Gly Leu Pro Phe Ile Lys Lys Ala Gly
            100                 105                 110

Val Glu His Lys Ile Asp Phe Ile Glu Ser Pro Ala Leu Pro Val Leu
        115                 120                 125

Asp Lys Leu Val Glu Asp Pro Ser Asn Lys Glu Ser Phe Asp Phe Ala
    130                 135                 140

Phe Val Asp Ala Asp Lys Asp Asn Tyr Trp Asn Tyr His Glu Arg Leu
145                 150                 155                 160

Leu Lys Leu Val Lys Ile Gly Gly Leu Ile Ile Tyr Asp Asn Thr Leu
                165                 170                 175

Trp Gly Gly Thr Val Ala Trp Pro Glu Glu Asp Val Pro Val Pro Lys
            180                 185                 190

Arg Lys Phe Arg Gln Ala Thr Leu Ala Phe Asn Lys Ala Ile Ala Asp
        195                 200                 205

Asp Ser Arg Val Glu Ile Ser Val Val Ser Ile Gly Asp Gly Phe Thr
    210                 215                 220

Ile Cys Arg Arg Ala His
225                 230
```

<210> SEQ ID NO 33
<211> LENGTH: 528
<212> TYPE: DNA
<213> ORGANISM: Glycine max
<220> FEATURE:
<221> NAME/KEY: unsure
<222> LOCATION: (401)
<220> FEATURE:
<221> NAME/KEY: unsure
<222> LOCATION: (408)
<220> FEATURE:
<221> NAME/KEY: unsure
<222> LOCATION: (440)
<220> FEATURE:
<221> NAME/KEY: unsure
<222> LOCATION: (442)
<220> FEATURE:
<221> NAME/KEY: unsure
<222> LOCATION: (460)

```
<220> FEATURE:
<221> NAME/KEY: unsure
<222> LOCATION: (465)
<220> FEATURE:
<221> NAME/KEY: unsure
<222> LOCATION: (473)
<220> FEATURE:
<221> NAME/KEY: unsure
<222> LOCATION: (491)
<220> FEATURE:
<221> NAME/KEY: unsure
<222> LOCATION: (494)
<220> FEATURE:
<221> NAME/KEY: unsure
<222> LOCATION: (513)
<220> FEATURE:
<221> NAME/KEY: unsure
<222> LOCATION: (523)
<220> FEATURE:
<221> NAME/KEY: unsure
<222> LOCATION: (526)..(527)

<400> SEQUENCE: 33
gatatataca gtatatcgta tacgctgcag tttgattgca ttttacttca accatgtcgg      60
gtgatttagc atacaagagc attctccaga gttcagcact tatgaagtac atctttgaaa    120
cgagtgccta tccaaaagag catgaacaat taaagctact cagagagacc acggtacaga    180
agtgccagga aaattcggaa tatatcatga atgtgccagt ggatgaagcg cagttcgtat    240
ctattctgct aaaatcatg aatgcgaaga aaacactgga aattggagta ttcactggct     300
attctcttct tgccacagct cttgctctgc ctcatgatgg caagataaca gcaattgatg    360
taaatagaaa aacatacgag attggattgc cattcattca naaggcanga atggagcaca    420
aaattgactt tatccttggn gntgcattat cagttctcan cgatncttat tantggtaag    480
caatgaggcc ncanttgcct aaggttattt gtnggatgcc ggntanng               528

<210> SEQ ID NO 34
<211> LENGTH: 137
<212> TYPE: PRT
<213> ORGANISM: Glycine max
<220> FEATURE:
<221> NAME/KEY: UNSURE
<222> LOCATION: (116)
<220> FEATURE:
<221> NAME/KEY: UNSURE
<222> LOCATION: (119)
<220> FEATURE:
<221> NAME/KEY: UNSURE
<222> LOCATION: (130)
<220> FEATURE:
<221> NAME/KEY: UNSURE
<222> LOCATION: (136)

<400> SEQUENCE: 34

Met Ser Gly Asp Leu Ala Tyr Lys Ser Ile Leu Gln Ser Ser Ala Leu
  1               5                  10                  15

Met Lys Tyr Ile Phe Glu Thr Ser Ala Tyr Pro Lys Glu His Glu Gln
                 20                  25                  30

Leu Lys Leu Leu Arg Glu Thr Thr Val Gln Lys Cys Gln Glu Asn Ser
             35                  40                  45

Glu Tyr Ile Met Asn Val Pro Val Asp Glu Ala Gln Phe Val Ser Ile
         50                  55                  60

Leu Leu Lys Ile Met Asn Ala Lys Lys Thr Leu Glu Ile Gly Val Phe
 65                  70                  75                  80

Thr Gly Tyr Ser Leu Leu Ala Thr Ala Leu Ala Leu Pro His Asp Gly
                 85                  90                  95
```

```
Lys Ile Thr Ala Ile Asp Val Asn Arg Lys Thr Tyr Glu Ile Gly Leu
            100                 105                 110

Pro Phe Ile Xaa Lys Ala Xaa Met Glu His Lys Ile Asp Phe Ile Leu
        115                 120                 125

Gly Xaa Ala Leu Ser Val Leu Xaa Asp
    130                 135
```

```
<210> SEQ ID NO 35
<211> LENGTH: 1018
<212> TYPE: DNA
<213> ORGANISM: Triticum aestivum
<220> FEATURE:
<221> NAME/KEY: unsure
<222> LOCATION: (817)
<220> FEATURE:
<221> NAME/KEY: unsure
<222> LOCATION: (826)
<220> FEATURE:
<221> NAME/KEY: unsure
<222> LOCATION: (874)
<220> FEATURE:
<221> NAME/KEY: unsure
<222> LOCATION: (891)
<220> FEATURE:
<221> NAME/KEY: unsure
<222> LOCATION: (924)
<220> FEATURE:
<221> NAME/KEY: unsure
<222> LOCATION: (934)
<220> FEATURE:
<221> NAME/KEY: unsure
<222> LOCATION: (961)
<220> FEATURE:
<221> NAME/KEY: unsure
<222> LOCATION: (970)..(971)
<220> FEATURE:
<221> NAME/KEY: unsure
<222> LOCATION: (1012)

<400> SEQUENCE: 35
acccgacgcg ctagctagtt ctattgccgc accccagatc tccaggaggg actcgttcgt      60
tcagctaact acactgcacg caatggccac cacggcgacc gaggcggcgc cggcgcagga     120
gcagcaggcc aacggcaacg gcgagcagaa gacgcgccac tccgaggtcg gccacaagag     180
cctgctcaag agcgacgacc tgtaccagta catcctggac acgagcgtgt acccgcggga     240
gccggagagc atgaaggagc tgcgcgagat caccgccaag cacccatgga acctgatgac     300
cacctccgcc gacgagggcc agttcctcaa catgctcatc aagctcatcg cgccaagaa      360 gaccatggag atcggcgtct acaccggcta ctccctgctc gccaccgcgc tcgccatccc     420
cgacgacggc accatcttgg ccatggacat caaccgcgag aactacgagc tggggctgcc     480
gtgcatcgag aaggccggcg tggcgcacaa gatcgacttc gcgagggcc cggcgctgcc      540 cgtcctggac gcgctgctgg aggacgaggc caaccacggg accttcgact tcgtcttcgt     600
ggacgccgac aaggacaact acctcaacta ccacgagcgc ctcatgaagc tcgtcaaggt     660
cggcggcctc ctcggctacg acaacaccct ctggaacggc tccgtcgtgc tcccgccgga     720
ggccccaatg cgcaagtaca tccgctacta ccgcgacttc gtcctccgac ctcaaacaag     780
gcctcgccgc ccgaccagcg cgtccgagat ctgccantcc ccgtcnggcg acggcatcac     840
ctctgccgcc gcgccaagtt gaacacagaa cccncttccg ccgctccggc nataagacgc     900
ccaagaacaa gatttattta ttancccat ttgncttcc tgtcgcttcc ggtatccaaa       960
nctacctccn ngatccgtat aaattctccc aagacaaacg attatatggg anccctat     1018
```

<210> SEQ ID NO 36
<211> LENGTH: 259
<212> TYPE: PRT
<213> ORGANISM: Triticum aestivum
<220> FEATURE:
<221> NAME/KEY: UNSURE
<222> LOCATION: (245)

<400> SEQUENCE: 36

Met Ala Thr Thr Ala Thr Glu Ala Ala Pro Ala Gln Glu Gln Gln Ala
1               5                   10                  15

Asn Gly Asn Gly Glu Gln Lys Thr Arg His Ser Glu Val Gly His Lys
            20                  25                  30

Ser Leu Leu Lys Ser Asp Asp Leu Tyr Gln Tyr Ile Leu Asp Thr Ser
        35                  40                  45

Val Tyr Pro Arg Glu Pro Glu Ser Met Lys Glu Leu Arg Glu Ile Thr
    50                  55                  60

Ala Lys His Pro Trp Asn Leu Met Thr Thr Ser Ala Asp Glu Gly Gln
65                  70                  75                  80

Phe Leu Asn Met Leu Ile Lys Leu Ile Gly Ala Lys Lys Thr Met Glu
                85                  90                  95

Ile Gly Val Tyr Thr Gly Tyr Ser Leu Leu Ala Thr Ala Leu Ala Ile
            100                 105                 110

Pro Asp Asp Gly Thr Ile Leu Ala Met Asp Ile Asn Arg Glu Asn Tyr
        115                 120                 125

Glu Leu Gly Leu Pro Cys Ile Glu Lys Ala Gly Val Ala His Lys Ile
    130                 135                 140

Asp Phe Arg Glu Gly Pro Ala Leu Pro Val Leu Asp Ala Leu Leu Glu
145                 150                 155                 160

Asp Glu Ala Asn His Gly Thr Phe Asp Phe Val Phe Val Asp Ala Asp
                165                 170                 175

Lys Asp Asn Tyr Leu Asn Tyr His Glu Arg Leu Met Lys Leu Val Lys
            180                 185                 190

Val Gly Gly Leu Leu Gly Tyr Asp Asn Thr Leu Trp Asn Gly Ser Val
        195                 200                 205

Val Leu Pro Pro Glu Ala Pro Met Arg Lys Tyr Ile Arg Tyr Tyr Arg
    210                 215                 220

Asp Phe Val Leu Arg Pro Gln Thr Arg Pro Arg Pro Thr Ser Ala
225                 230                 235                 240

Ser Glu Ile Cys Xaa Ser Pro Ser Gly Asp Gly Ile Thr Ser Ala Ala
                245                 250                 255

Ala Pro Ser

<210> SEQ ID NO 37
<211> LENGTH: 1118
<212> TYPE: DNA
<213> ORGANISM: Triticum aestivum

<400> SEQUENCE: 37
gcacgagacc cgacgcgcta gctagttcta ttgccgcacc ccagatctcc aggagggact      60
cgttcgttca gctaactaca ctgcacgcaa tggccaccac ggcgaccgag gcggcgccgg     120
cgcaggagca gcaggccaac ggcaacggcg agcagaagac gcggcactcc gaggtcggcc     180
acaagagcct gctcaagagc gacgacctct accagtacat cctggacacg agcgtgtacc     240
cgcgggagcc ggagagcatg aaggagctcc gcgagatcac cgccaagcac ccatggaacc     300

-continued

```
tgatgacgac ctccgccgac gagggcagt tcctgaacat gctcatcaag ctcatcggcg      360
ccaagaagac catggagatc ggcgtctaca ccggctactc cctcctcgcc acggcgctcg      420
ccctcccgga ggacggcacg atcttggcca tggacatcaa ccgcgagaac tacgagctgg      480
gcctgccctg catcgagaag gccggcgtcg cccacaagat cgacttccgc gagggtcccg      540
cgctccccgt cctcgacgac ctcatcgcgg aggagaagaa ccacgggtcg ttcgacttcg      600
tcttcgtgga cgccgacaag gacaactacc tcaactacca cgagcggctg ctgaagctgg      660
tgaagctggg cggcctcatc ggctacgaca cacgctgtg aacggctcc gtcgtgctcc       720
ccgacgacgc gcccatgcgc aagtacatcc gcttctaccg cgacttcgtg ctcgtcctca      780
acaaggcgct cgccgccgac gaccgcgtcg agatctgcca gctccccgtc ggcgacggcg      840
tcaccctctg ccgccgcgtc aagtgaaaac atggcctggc ctggcctgcc ccaccaccgc      900
caccgacggc gccgccggcc gcatcctcat tccaatcata atagacgacc cgcagcatta      960
attatccacc ggcttttttt ttggctctt cttgcccctg taatctttct cctcctcttc      1020
cttcttggga attgtcgccg ccgtttcgat acgtaaatca cgagatcggt aatacagtaa      1080
tgctcctcaa ttttacaata aaaaaaaaaa aaaaaaaa                              1118
```

<210> SEQ ID NO 38
<211> LENGTH: 258
<212> TYPE: PRT
<213> ORGANISM: Triticum aestivum

<400> SEQUENCE: 38

```
Met Ala Thr Thr Ala Thr Glu Ala Ala Pro Ala Gln Glu Gln Gln Ala
  1               5                  10                  15

Asn Gly Asn Gly Glu Gln Lys Thr Arg His Ser Glu Val Gly His Lys
             20                  25                  30

Ser Leu Leu Lys Ser Asp Asp Leu Tyr Gln Tyr Ile Leu Asp Thr Ser
         35                  40                  45

Val Tyr Pro Arg Glu Pro Glu Ser Met Lys Glu Leu Arg Glu Ile Thr
     50                  55                  60

Ala Lys His Pro Trp Asn Leu Met Thr Thr Ser Ala Asp Glu Gly Gln
 65                  70                  75                  80

Phe Leu Asn Met Leu Ile Lys Leu Ile Gly Ala Lys Lys Thr Met Glu
                 85                  90                  95

Ile Gly Val Tyr Thr Gly Tyr Ser Leu Leu Ala Thr Ala Leu Ala Leu
            100                 105                 110

Pro Glu Asp Gly Thr Ile Leu Ala Met Asp Ile Asn Arg Glu Asn Tyr
        115                 120                 125

Glu Leu Gly Leu Pro Cys Ile Glu Lys Ala Gly Val Ala His Lys Ile
    130                 135                 140

Asp Phe Arg Glu Gly Pro Ala Leu Pro Val Leu Asp Asp Leu Ile Ala
145                 150                 155                 160

Glu Glu Lys Asn His Gly Ser Phe Asp Phe Val Phe Val Asp Ala Asp
                165                 170                 175

Lys Asp Asn Tyr Leu Asn Tyr His Glu Arg Leu Leu Lys Leu Val Lys
            180                 185                 190

Leu Gly Gly Leu Ile Gly Tyr Asp Asn Thr Leu Trp Asn Gly Ser Val
        195                 200                 205

Val Leu Pro Asp Asp Ala Pro Met Arg Lys Tyr Ile Arg Phe Tyr Arg
    210                 215                 220

Asp Phe Val Leu Val Leu Asn Lys Ala Leu Ala Ala Asp Asp Arg Val
```

```
225                 230                 235                 240
Glu Ile Cys Gln Leu Pro Val Gly Asp Gly Val Thr Leu Cys Arg Arg
                245                 250                 255

Val Lys

<210> SEQ ID NO 39
<211> LENGTH: 600
<212> TYPE: DNA
<213> ORGANISM: Triticum aestivum
<220> FEATURE:
<221> NAME/KEY: unsure
<222> LOCATION: (462)
<220> FEATURE:
<221> NAME/KEY: unsure
<222> LOCATION: (522)
<220> FEATURE:
<221> NAME/KEY: unsure
<222> LOCATION: (541)
<220> FEATURE:
<221> NAME/KEY: unsure
<222> LOCATION: (553)

<400> SEQUENCE: 39
ggctgcaggc tcgtgccgaa ttcggcacga gcaatcaccc acccaaccaa ccacctctgc      60
acgcgcagcc cagatctcgg ccccttccct tcctcggacc aagcaccagc aatggccacc     120
acggcagccg acgccacggc cgcggcgccc aaggaccagc ccgccaacgg ttccgagcag     180
gtcacgcgcc actccgaggt cggccacaag agcctgctcc agagcgacgc cctctaccag     240
tacatcctgg agacgagcgt gtacccgcgc gagcacgagt gcatgaagga gctccgcgag     300
atcaccgcca accacccatg gaacctgatg acgacgtcgg cggacgaggg ccagttcctc     360
aacatgctgc tcaagctcat cggcgccaag aagaccatgg agatcggcgt ctacaccggc     420
tactccctcc tcgccaacgc gctcgccatc cccgacgacg gnacatcttg gcatggacat     480
caaccgcgag aactacaact ggggctgccg tgcatcgaga angccgggtg gcgcacaagt     540
ngacttcggc ganggcccgc gctgcggtgt ggaccccctgt ggaggacagg caacaacgac     600

<210> SEQ ID NO 40
<211> LENGTH: 131
<212> TYPE: PRT
<213> ORGANISM: Triticum aestivum
<220> FEATURE:
<221> NAME/KEY: UNSURE
<222> LOCATION: (118)

<400> SEQUENCE: 40

Met Ala Thr Thr Ala Ala Asp Ala Thr Ala Ala Ala Pro Lys Asp Gln
  1               5                  10                  15

Pro Ala Asn Gly Ser Glu Gln Val Thr Arg His Ser Glu Val Gly His
                 20                  25                  30

Lys Ser Leu Leu Gln Ser Asp Ala Leu Tyr Gln Tyr Ile Leu Glu Thr
             35                  40                  45

Ser Val Tyr Pro Arg Glu His Glu Cys Met Lys Glu Leu Arg Glu Ile
         50                  55                  60

Thr Ala Asn His Pro Trp Asn Leu Met Thr Thr Ser Ala Asp Glu Gly
 65                  70                  75                  80

Gln Phe Leu Asn Met Leu Leu Lys Leu Ile Gly Ala Lys Lys Thr Met
                 85                  90                  95

Glu Ile Gly Val Tyr Thr Gly Tyr Ser Leu Leu Ala Asn Ala Leu Ala
                100                 105                 110
```

Ile Pro Asp Asp Gly Xaa Leu Gly Met Asp Ile Asn Arg Glu Asn Tyr
        115                 120                 125

Asn Trp Gly
        130

<210> SEQ ID NO 41
<211> LENGTH: 1078
<212> TYPE: DNA
<213> ORGANISM: Triticum aestivum

<400> SEQUENCE: 41

| | | | | | |
|---|---|---|---|---|---|
| ctcgtgccga | attcggcacg | agcaatcacc | cacccaacca | accacctctg | cacgcgcagc | 60 |
| ccagatctcg | gccccttccc | ttcctcggac | caagcaccag | caatggccac | acggcagcc | 120 |
| gacgccacgg | ccgcggcgcc | caaggaccag | cccgccaacg | gttccgagca | ggtcacgcgc | 180 |
| cactccgagg | tcggccacaa | gagcctgctc | cagagcgacg | ccctctacca | gtacatcctg | 240 |
| gagacgagcg | tgtacccgcg | cgagcacgag | tgcatgaagg | agctccgcga | gatcaccgcc | 300 |
| aaccacccat | ggaacctgat | gacgacgtcg | gcggacgagg | gccagttcct | caacatgctg | 360 |
| ctcaagctca | tcggcgccaa | gaagaccatg | gagatcggcg | tctacaccgg | ctactccctc | 420 |
| ctcgccaccg | cgctcgccat | ccccgacgac | ggcaccatct | ggccatgga | catcaaccgc | 480 |
| gagaactacg | agctggggct | gccgtgcatc | gagaaggccg | cgtggcgca | caagatcgac | 540 |
| ttccgcgagg | gccggcgct | gccggtgctg | gacgcgctgc | tggaggacga | ggccaaccac | 600 |
| ggcaccttcg | acttcgtctt | cgtggacgcc | gacaaggaca | actacctcaa | ctaccacgag | 660 |
| cgcctcatga | agctcgtcaa | gctcggcggc | ctcctcggct | acgacaacac | gctctggaac | 720 |
| ggctccgtcg | tgctccccgc | cgacgccccc | atgcgcaagt | acatccgcta | ctaccgcgac | 780 |
| ttcgtcctcg | acctcaacaa | ggccctcgcc | gccgaccagc | gcgtcgagat | ctgccagctc | 840 |
| cccgtcggcg | acggcatcac | cctctgccgc | gcgccaagt | gaaccacaga | acccgtctcc | 900 |
| gccgctccgc | catagacgcc | aagaacaaga | attaattaat | tactcccat | tttgtctttc | 960 |
| ctgctcgcct | tctgtactct | atatctatct | tctgcaattc | gtataaagat | ttctccagac | 1020 |
| aaacgattaa | tattggtact | ccaaaaaaaa | aaaaaaaaa | aaaaaaaaa | aaaaaaa | 1078 |

<210> SEQ ID NO 42
<211> LENGTH: 259
<212> TYPE: PRT
<213> ORGANISM: Triticum aestivum

<400> SEQUENCE: 42

Met Ala Thr Thr Ala Ala Asp Ala Thr Ala Ala Ala Pro Lys Asp Gln
  1               5                  10                  15

Pro Ala Asn Gly Ser Glu Gln Val Thr Arg His Ser Glu Val Gly His
                20                  25                  30

Lys Ser Leu Leu Gln Ser Asp Ala Leu Tyr Gln Tyr Ile Leu Glu Thr
            35                  40                  45

Ser Val Tyr Pro Arg Glu His Glu Cys Met Lys Glu Leu Arg Glu Ile
        50                  55                  60

Thr Ala Asn His Pro Trp Asn Leu Met Thr Thr Ser Ala Asp Glu Gly
    65                  70                  75                  80

Gln Phe Leu Asn Met Leu Leu Lys Leu Ile Gly Ala Lys Lys Thr Met
                85                  90                  95

Glu Ile Gly Val Tyr Thr Gly Tyr Ser Leu Leu Ala Thr Ala Leu Ala
                100                 105                 110

```
Ile Pro Asp Asp Gly Thr Ile Leu Ala Met Asp Ile Asn Arg Glu Asn
        115                 120                 125
Tyr Glu Leu Gly Leu Pro Cys Ile Glu Lys Ala Gly Val Ala His Lys
130                 135                 140
Ile Asp Phe Arg Glu Gly Pro Ala Leu Pro Val Leu Asp Ala Leu Leu
145                 150                 155                 160
Glu Asp Glu Ala Asn His Gly Thr Phe Asp Phe Val Phe Val Asp Ala
                165                 170                 175
Asp Lys Asp Asn Tyr Leu Asn Tyr His Glu Arg Leu Met Lys Leu Val
            180                 185                 190
Lys Leu Gly Gly Leu Leu Gly Tyr Asp Asn Thr Leu Trp Asn Gly Ser
        195                 200                 205
Val Val Leu Pro Ala Asp Ala Pro Met Arg Lys Tyr Ile Arg Tyr Tyr
    210                 215                 220
Arg Asp Phe Val Leu Asp Leu Asn Lys Ala Leu Ala Ala Asp Gln Arg
225                 230                 235                 240
Val Glu Ile Cys Gln Leu Pro Val Gly Asp Gly Ile Thr Leu Cys Arg
                245                 250                 255
Arg Ala Lys

<210> SEQ ID NO 43
<211> LENGTH: 1049
<212> TYPE: DNA
<213> ORGANISM: Triticum aestivum
<220> FEATURE:
<221> NAME/KEY: unsure
<222> LOCATION: (352)
<220> FEATURE:
<221> NAME/KEY: unsure
<222> LOCATION: (948)
<220> FEATURE:
<221> NAME/KEY: unsure
<222> LOCATION: (992)
<220> FEATURE:
<221> NAME/KEY: unsure
<222> LOCATION: (994)
<220> FEATURE:
<221> NAME/KEY: unsure
<222> LOCATION: (999)
<220> FEATURE:
<221> NAME/KEY: unsure
<222> LOCATION: (1003)
<220> FEATURE:
<221> NAME/KEY: unsure
<222> LOCATION: (1038)

<400> SEQUENCE: 43
cgaaccaacc cattcctcct actacctcgg cacaaccagc ccaaacagaa ctagcgagca     60
gagccatggc gcccaacgga gacaacaccg tggccaacgt ccacagcggc atcgacagca    120
ccaacaagac gctgctcaag agcgacgccc tctacactta catcctcgac accaccgtgt    180
tcccccgcga gcacgagtgc atgcgcgacc tgcgcctcat caccgacaag cacccatggg    240
gttacatgca gtcgtcctcg gacgaggcgc agctgctggg gatgctgatc aagatggcgg    300
gcgccaagaa gacgatcgag gtgggcgtgt tcacgggcta ctcgctgctg gncaccgcgc    360
tggcgctccc ggaggacggc aaggtggtgg gcatcgacac cgaccgcgag tgctacgagg    420
tgggtcgccc cttcattgag aaggccggca tggcgcacaa ggtggacttc cgcgagggca    480
ccggcctggc gcgcctggac gagctcctcg tcgaggacga cggcgcggcg agctacgact    540
tcgcgttcgt ggacgcggac aagcccaact acgtgcgcta ccacgagcag ctgctgaagc    600
tggtccgcgt cggcggcact atcatctacg acaacacgct ctgggcggc acggtggcgc    660
```

```
tgccggcggg caccccatg tccgacctcg acacccgctt ctccgccgcc ctcagggacc      720
tcaacgccaa gctcgccgcc gacccgcgca tcgaggtctg ccagctcgcc atcgccgacg      780
gcgtcaccat ctgccgccgc atcgtctaga cgggcgtccg gcccggcccg gcgtgatcgt      840
gattcgccgt gcgcctgcgg cctgcgtgcg tgcgtggagt ccatttctta ccagccgtta      900
tcttaatcaa ttgtattatt tttttccctg cagcgctggc gcgtgaanat ctgatggttg      960
aaatttcaat aatattttttg gctttaattt anangagang gangattgct gtacttatga     1020
atgtaatata ctaaaatngt gttcgatgt                                        1049
```

<210> SEQ ID NO 44
<211> LENGTH: 247
<212> TYPE: PRT
<213> ORGANISM: Triticum aestivum
<220> FEATURE:
<221> NAME/KEY: UNSURE
<222> LOCATION: (96)

<400> SEQUENCE: 44

```
Met Ala Pro Asn Gly Asp Asn Thr Val Ala Asn Val His Ser Gly Ile
 1               5                  10                  15

Asp Ser Thr Asn Lys Thr Leu Leu Lys Ser Asp Ala Leu Tyr Thr Tyr
            20                  25                  30

Ile Leu Asp Thr Thr Val Phe Pro Arg Glu His Glu Cys Met Arg Asp
        35                  40                  45

Leu Arg Leu Ile Thr Asp Lys His Pro Trp Gly Tyr Met Gln Ser Ser
    50                  55                  60

Ser Asp Glu Ala Gln Leu Leu Gly Met Leu Ile Lys Met Ala Gly Ala
65                  70                  75                  80

Lys Lys Thr Ile Glu Val Gly Val Phe Thr Gly Tyr Ser Leu Leu Xaa
                85                  90                  95

Thr Ala Leu Ala Leu Pro Glu Asp Gly Lys Val Val Gly Ile Asp Thr
            100                 105                 110

Asp Arg Glu Cys Tyr Glu Val Gly Arg Pro Phe Ile Glu Lys Ala Gly
        115                 120                 125

Met Ala His Lys Val Asp Phe Arg Glu Gly Thr Gly Leu Ala Arg Leu
    130                 135                 140

Asp Glu Leu Leu Val Glu Asp Asp Gly Ala Ala Ser Tyr Asp Phe Ala
145                 150                 155                 160

Phe Val Asp Ala Asp Lys Pro Asn Tyr Val Arg Tyr His Glu Gln Leu
                165                 170                 175

Leu Lys Leu Val Arg Val Gly Gly Thr Ile Ile Tyr Asp Asn Thr Leu
            180                 185                 190

Trp Gly Gly Thr Val Ala Leu Pro Ala Gly Thr Pro Met Ser Asp Leu
        195                 200                 205

Asp Thr Arg Phe Ser Ala Ala Leu Arg Asp Leu Asn Ala Lys Leu Ala
    210                 215                 220

Ala Asp Pro Arg Ile Glu Val Cys Gln Leu Ala Ile Ala Asp Gly Val
225                 230                 235                 240

Thr Ile Cys Arg Arg Ile Val
                245
```

<210> SEQ ID NO 45
<211> LENGTH: 953
<212> TYPE: DNA
<213> ORGANISM: Triticum aestivum

<400> SEQUENCE: 45

```
cgaaccaacc cattcctcct actacctcgg cacaaccagc ccaaacagaa ctagcgagca      60
gagccatggc gcccaacgga gacaacaccg tggccaacgt ccacagcggc atcgacagca     120
ccaacaagac gctgctcaag agcgacgccc tctacactta catcctcgac accaccgtgt     180
tcccccgcga gcacgagtgc atgcgcgacc tgcgcctcat caccgacaag cacccatggg     240
gttacatgca gtcgtcctcg gacgaggcgc agctgctggg gatgctgatc aagatggcgg     300
gcgccaagaa gacgatcgag gtgggcgtgt tcacgggcta ctcgctgctg ccaccgcgc      360
tggcgctccc ggaggacggc aaggtggtgg ccatcgacac cgaccgcgag tgctacgagg     420
tgggtcgccc cttcatcgag aaggccggca tggcgcacaa ggtggacttc gcgagggca      480
ccggcctggc gcgcctggac gagctcctcg tcgaggacga cggcgcggcg agctacgact     540
tcgcgttcgt ggacgcggac aagcccaact acgtgcgcta ccacgagcag ctgctgaagc     600
tggtccgcgt cggcggcact atcatctacg acaacacgct ctgggcggc acggtggcgc     660
tgccggcggg cacccccatg tccgacctcg acacccgctt ctccgccgcc ctcagggacc     720
tcaacgccaa gctcgccgcc gacccgcgca tcgaggtctg ccagctcgcc atcgccgacg     780
gagtcaccat ctgccgccgc atcgtctagg cgggcgggcg tccggcccgg cccggcgtga     840
tcgtgatccg ccgcgcgcct gccggcctgc gtgcgtgcgt ggagtccatt tccttaccag     900
ccgcttatct taatcaattg tattattatt tttccaaaaa aaaaaaaaaa aaa            953
```

<210> SEQ ID NO 46
<211> LENGTH: 247
<212> TYPE: PRT
<213> ORGANISM: Triticum aestivum

<400> SEQUENCE: 46

```
Met Ala Pro Asn Gly Asp Asn Thr Val Ala Asn Val His Ser Gly Ile
  1               5                  10                  15

Asp Ser Thr Asn Lys Thr Leu Leu Lys Ser Asp Ala Leu Tyr Thr Tyr
             20                  25                  30

Ile Leu Asp Thr Thr Val Phe Pro Arg Glu His Glu Cys Met Arg Asp
         35                  40                  45

Leu Arg Leu Ile Thr Asp Lys His Pro Trp Gly Tyr Met Gln Ser Ser
     50                  55                  60

Ser Asp Glu Ala Gln Leu Leu Gly Met Leu Ile Lys Met Ala Gly Ala
 65                  70                  75                  80

Lys Lys Thr Ile Glu Val Gly Val Phe Thr Gly Tyr Ser Leu Leu Ala
                 85                  90                  95

Thr Ala Leu Ala Leu Pro Glu Asp Gly Lys Val Val Ala Ile Asp Thr
            100                 105                 110

Asp Arg Glu Cys Tyr Glu Val Gly Arg Pro Phe Ile Glu Lys Ala Gly
        115                 120                 125

Met Ala His Lys Val Asp Phe Arg Glu Gly Thr Gly Leu Ala Arg Leu
    130                 135                 140

Asp Glu Leu Leu Val Glu Asp Asp Gly Ala Ala Ser Tyr Asp Phe Ala
145                 150                 155                 160

Phe Val Asp Ala Asp Lys Pro Asn Tyr Val Arg Tyr His Glu Gln Leu
                165                 170                 175

Leu Lys Leu Val Arg Val Gly Gly Thr Ile Ile Tyr Asp Asn Thr Leu
            180                 185                 190
```

```
Trp Gly Gly Thr Val Ala Leu Pro Ala Gly Thr Pro Met Ser Asp Leu
            195                 200                 205

Asp Thr Arg Phe Ser Ala Ala Leu Arg Asp Leu Asn Ala Lys Leu Ala
        210                 215                 220

Ala Asp Pro Arg Ile Glu Val Cys Gln Leu Ala Ile Ala Asp Gly Val
225                 230                 235                 240

Thr Ile Cys Arg Arg Ile Val
                245
```

<210> SEQ ID NO 47
<211> LENGTH: 534
<212> TYPE: DNA
<213> ORGANISM: Triticum aestivum
<220> FEATURE:
<221> NAME/KEY: unsure
<222> LOCATION: (530)

<400> SEQUENCE: 47

```
cttttttag tcggtgcgtg tgtgtgcgcg cgcgcatttc gctcgttcat agacatggct      60
tccaacggga gcgccggcga ggtcagggat gtccacagca gcgagaccac caagaccctc    120
ctcaagagca acgacctcta cgattacatg ttgaagacga tggtgtaccc gcgggagaac    180
gagttcatgc gcgagctccg acagatcacc aacgagcaca tcttcgggtt catgtcgtcg    240
ccgccggacg agggctggt gctgtcgctg ctgctcaagc tgatgggcgc caagaggacc    300
atcgaggtcg ggtctacac cggctgctcc gtcctcgcta ccgcgctcgc catcccggac    360
gacggcagga tcgtcgccat cgacgtcagc agggagtact cgacctcgg cctccccgtc    420
atcaagaagg ccggcgtcgc gcacaaggtc gacttccgcg agggcccgc cggccccatc    480
ctcgacaagc tcatcgccga cgaggacgaa ggggagcttc gacttcgccn tcgg         534
```

<210> SEQ ID NO 48
<211> LENGTH: 145
<212> TYPE: PRT
<213> ORGANISM: Triticum aestivum

<400> SEQUENCE: 48

```
Met Ala Ser Asn Gly Ser Ala Gly Glu Val Arg Asp Val His Ser Ser
  1               5                  10                  15

Glu Thr Thr Lys Thr Leu Leu Lys Ser Asn Asp Leu Tyr Asp Tyr Met
             20                  25                  30

Leu Lys Thr Met Val Tyr Pro Arg Glu Asn Glu Phe Met Arg Glu Leu
         35                  40                  45

Arg Gln Ile Thr Asn Glu His Ile Phe Gly Phe Met Ser Ser Pro Pro
     50                  55                  60

Asp Glu Gly Leu Val Leu Ser Leu Leu Leu Lys Leu Met Gly Ala Lys
 65                  70                  75                  80

Arg Thr Ile Glu Val Gly Val Tyr Thr Gly Cys Ser Val Leu Ala Thr
                 85                  90                  95

Ala Leu Ala Ile Pro Asp Asp Gly Arg Ile Val Ala Ile Asp Val Ser
            100                 105                 110

Arg Glu Tyr Phe Asp Leu Gly Leu Pro Val Ile Lys Lys Ala Gly Val
        115                 120                 125

Ala His Lys Val Asp Phe Arg Glu Gly Pro Ala Gly Pro Ile Leu Asp
    130                 135                 140

Lys
145
```

```
<210> SEQ ID NO 49
<211> LENGTH: 258
<212> TYPE: PRT
<213> ORGANISM: Zea mays

<400> SEQUENCE: 49

Met Ala Thr Thr Ala Thr Glu Ala Ala Pro Ala Gln Glu Gln Gln Ala
  1               5                  10                  15

Asn Gly Asn Gly Glu Gln Lys Thr Arg His Ser Glu Val Gly His Lys
             20                  25                  30

Ser Leu Leu Lys Ser Asp Asp Leu Tyr Gln Tyr Ile Leu Asp Thr Ser
         35                  40                  45

Val Tyr Pro Arg Glu Pro Glu Ser Met Lys Glu Leu Arg Glu Val Thr
 50                  55                  60

Ala Lys His Pro Trp Asn Leu Met Thr Thr Ser Ala Asp Glu Gly Gln
 65                  70                  75                  80

Phe Leu Asn Met Leu Ile Lys Leu Ile Gly Ala Lys Lys Thr Met Glu
                 85                  90                  95

Ile Gly Val Tyr Thr Gly Tyr Ser Leu Leu Ala Thr Ala Leu Ala Leu
            100                 105                 110

Pro Glu Asp Gly Thr Ile Leu Ala Met Asp Ile Asn Arg Glu Asn Tyr
        115                 120                 125

Glu Leu Gly Leu Pro Cys Ile Glu Lys Ala Gly Val Ala His Lys Ile
130                 135                 140

Asp Phe Arg Glu Gly Pro Ala Leu Pro Val Leu Asp Asp Leu Ile Ala
145                 150                 155                 160

Glu Glu Lys Asn His Gly Ser Phe Asp Phe Val Phe Val Asp Ala Asp
                165                 170                 175

Lys Asp Asn Tyr Leu Asn Tyr His Glu Arg Leu Leu Lys Leu Val Lys
            180                 185                 190

Leu Gly Gly Leu Ile Gly Tyr Asp Asn Thr Leu Trp Asn Gly Ser Val
        195                 200                 205

Val Leu Pro Asp Asp Ala Pro Met Arg Lys Tyr Ile Arg Phe Tyr Arg
    210                 215                 220

Asp Phe Val Leu Val Leu Asn Lys Ala Leu Ala Ala Asp Asp Arg Val
225                 230                 235                 240

Glu Ile Cys Gln Leu Pro Val Gly Asp Gly Val Thr Leu Cys Arg Arg
                245                 250                 255

Val Lys

<210> SEQ ID NO 50
<211> LENGTH: 247
<212> TYPE: PRT
<213> ORGANISM: Populus tremuloides

<400> SEQUENCE: 50

Met Ala Thr Asn Gly Glu Glu Gln Gln Ser Gln Ala Gly Arg His Gln
  1               5                  10                  15

Glu Val Gly His Lys Ser Leu Leu Gln Ser Asp Ala Leu Tyr Gln Tyr
             20                  25                  30

Ile Leu Glu Thr Ser Val Tyr Pro Arg Glu Pro Glu Cys Met Lys Glu
         35                  40                  45

Leu Arg Glu Val Thr Ala Lys His Pro Trp Asn Ile Met Thr Thr Ser
 50                  55                  60

Ala Asp Glu Gly Gln Phe Leu Asn Met Leu Leu Lys Leu Val Asn Ala
```

-continued

```
            65                  70                  75                  80
Lys Asn Thr Met Glu Ile Gly Val Tyr Thr Gly Tyr Ser Leu Leu Ala
                85                  90                  95

Thr Ala Leu Ala Ile Pro Glu Asp Gly Lys Ile Leu Ala Met Asp Ile
               100                 105                 110

Asn Arg Glu Asn Tyr Glu Leu Gly Leu Pro Val Ile Gln Lys Ala Gly
               115                 120                 125

Val Ala His Lys Ile Asp Phe Lys Glu Gly Pro Ala Leu Pro Val Leu
               130                 135                 140

Asp Gln Met Ile Glu Asp Gly Lys Tyr His Gly Ser Phe Asp Phe Ile
145                 150                 155                 160

Phe Val Asp Ala Asp Lys Asp Asn Tyr Ile Asn Tyr His Lys Arg Leu
               165                 170                 175

Ile Glu Leu Val Lys Val Gly Gly Leu Ile Gly Tyr Asp Asn Thr Leu
               180                 185                 190

Trp Asn Gly Ser Val Val Ala Pro Pro Asp Ala Pro Met Arg Lys Tyr
           195                 200                 205

Val Arg Tyr Tyr Arg Asp Phe Val Leu Glu Leu Asn Lys Ala Leu Ala
           210                 215                 220

Ala Asp Pro Arg Ile Glu Ile Cys Met Leu Pro Val Gly Asp Gly Ile
225                 230                 235                 240

Thr Leu Cys Arg Arg Ile Gln
                245
```